(12) United States Patent
Kester et al.

(10) Patent No.: US 10,458,905 B2
(45) Date of Patent: Oct. 29, 2019

(54) GAS LEAK EMISSION QUANTIFICATION WITH A GAS CLOUD IMAGER

(71) Applicant: REBELLION PHOTONICS, INC., Houston, TX (US)

(72) Inventors: Robert Timothy Kester, Pearland, TX (US); Nathan Adrian Hagen, Houston, TX (US); Ryan Mallery, Houston, TX (US)

(73) Assignee: Rebellion Photonics, Inc., Houston, TX (US)

(*) Notice: Subject to any disclaimer, the term of this patent is extended or adjusted under 35 U.S.C. 154(b) by 28 days.

(21) Appl. No.: 14/792,477

(22) Filed: Jul. 6, 2015

(65) Prior Publication Data

US 2016/0097713 A1  Apr. 7, 2016

Related U.S. Application Data

(60) Provisional application No. 62/021,636, filed on Jul. 7, 2014, provisional application No. 62/021,907, filed on (Continued)

(51) Int. Cl.
*G01J 3/00* (2006.01)
*G01N 21/3504* (2014.01)
(Continued)

(52) U.S. Cl.
CPC .......... *G01N 21/3504* (2013.01); *G01M 3/26* (2013.01); *G01M 3/38* (2013.01); *G01N 2021/1793* (2013.01); *G01N 2021/3531* (2013.01)

(58) Field of Classification Search
CPC ... G01N 2021/1793; G01N 2021/3531; G01N 21/3504
(Continued)

(56) References Cited

U.S. PATENT DOCUMENTS 3,841,763 A  10/1974 Lewis
3,849,005 A  11/1974 Girard et al.
(Continued)

FOREIGN PATENT DOCUMENTS

CA  2 365 866   9/2000
CA  2 787 303   7/2011
(Continued)

OTHER PUBLICATIONS

US 10,113,914 B2, 10/2018, Kester et al. (withdrawn)
(Continued)

*Primary Examiner* — Sunghee Y Gray
(74) *Attorney, Agent, or Firm* — Knobbe, Martens, Olson & Bear, LLP

(57) ABSTRACT

An instrument and method for analyzing a gas leak. The instrument can obtain a time series of spectra from a scene. The instrument can compare spectra from different times to determine a property of a gas cloud within the scene. The instrument can estimate the column density of the gas cloud at one or more locations within the scene. The instrument can estimate the total quantity of gas in the cloud. The instrument can estimate the amount of gas which has left the field of view of the instrument. The instrument can also estimate the amount of gas in the cloud which has dropped below the sensitivity limit of the instrument.

25 Claims, 15 Drawing Sheets

Related U.S. Application Data on Jul. 8, 2014, provisional application No. 62/083,131, filed on Nov. 21, 2014.

(51) Int. Cl.
G01M 3/26 (2006.01)
G01M 3/38 (2006.01)
G01N 21/17 (2006.01)

(58) Field of Classification Search
USPC .......................................................... 356/51
See application file for complete search history.

(56) References Cited

U.S. PATENT DOCUMENTS

| | | | |
|---|---|---|---|
| 4,134,683 A | 1/1979 | Goetz et al. | |
| 4,464,789 A | 8/1984 | Sternberg | |
| 4,933,555 A | 6/1990 | Smith | |
| 4,963,963 A | 10/1990 | Dorman | |
| 5,127,742 A | 7/1992 | Fraden | |
| 5,136,421 A | 8/1992 | Sagan | |
| 5,157,258 A | 10/1992 | Gunning, III et al. | |
| 5,354,987 A | 10/1994 | MacPherson | |
| 5,550,373 A | 8/1996 | Cole et al. | |
| 5,559,336 A | 9/1996 | Kosai et al. | |
| 5,604,346 A | 2/1997 | Hamrelius et al. | |
| 5,822,222 A | 10/1998 | Kaplinsky et al. | |
| 5,877,500 A | 3/1999 | Braig et al. | |
| 5,920,066 A | 7/1999 | DiRenzo et al. | |
| 5,926,283 A | 7/1999 | Hopkins | |
| 5,973,844 A | 10/1999 | Burger | |
| 5,994,701 A | 11/1999 | Tsuchimoto et al. | |
| 6,023,061 A | 2/2000 | Bodkin | |
| 6,097,034 A | 8/2000 | Weckström | |
| 6,184,529 B1 | 2/2001 | Contini | |
| 6,268,883 B1 | 7/2001 | Zehnder et al. | |
| 6,456,261 B1 | 9/2002 | Zhang | |
| 6,465,785 B1 | 10/2002 | McManus | |
| 6,556,853 B1* | 4/2003 | Cabib ................ A61B 5/14555 351/221 | |
| 6,680,778 B2 | 1/2004 | Hinnrichs et al. | |
| 6,700,527 B1 | 3/2004 | Martin et al. | |
| 7,109,488 B2 | 9/2006 | Milton | |
| 7,119,337 B1 | 10/2006 | Johnson et al. | |
| 7,242,478 B1 | 7/2007 | Dombrowski et al. | |
| 7,315,377 B2 | 1/2008 | Holland et al. | |
| 7,321,119 B2 | 1/2008 | King | |
| 7,364,697 B2 | 4/2008 | McFarland et al. | |
| 7,433,042 B1 | 10/2008 | Cavanaugh et al. | |
| 7,606,484 B1 | 10/2009 | Richards et al. | |
| 7,634,157 B1 | 12/2009 | Richards et al. | |
| 7,750,802 B1 | 7/2010 | Parish et al. | |
| 7,835,002 B2 | 11/2010 | Muhammed et al. | |
| 7,888,624 B1 | 2/2011 | Murguia et al. | |
| 8,027,041 B1 | 9/2011 | Mitchell et al. | |
| 8,153,980 B1 | 4/2012 | Brady et al. | |
| 8,159,568 B2 | 4/2012 | Ahdoot | |
| 8,212,213 B2 | 7/2012 | Myrick et al. | |
| 8,373,757 B1 | 2/2013 | Nguyen | |
| 8,629,930 B2 | 1/2014 | Brueckner et al. | |
| 8,653,461 B1 | 2/2014 | Benson et al. | |
| 8,654,328 B2 | 2/2014 | Tkaczyk et al. | |
| 8,686,364 B1 | 4/2014 | Little et al. | |
| 9,395,516 B2 | 7/2016 | Katsunuma et al. | |
| 9,562,849 B2 | 2/2017 | Kester et al. | |
| 9,599,508 B2 | 3/2017 | Kester et al. | |
| 9,625,318 B2 | 4/2017 | Kester et al. | |
| 9,641,772 B2 | 5/2017 | Yujiri | |
| 9,644,562 B2 | 5/2017 | Fujita | |
| 9,756,263 B2 | 9/2017 | Kester et al. | |
| 10,084,975 B2 | 9/2018 | Kester et al. | |
| 10,254,166 B2 | 4/2019 | Kester et al. | |
| 10,267,686 B2 | 4/2019 | Kester et al. | |
| 2001/0040216 A1 | 11/2001 | Knauth et al. | |
| 2002/0015151 A1 | 2/2002 | Gorin | |
| 2002/0121370 A1 | 9/2002 | Kurkjian et al. | |
| 2002/0159101 A1 | 10/2002 | Alderson et al. | |
| 2003/0102435 A1 | 6/2003 | Myers et al. | |
| 2003/0134426 A1 | 7/2003 | Jiang et al. | |
| 2003/0183756 A1 | 10/2003 | Huniu | |
| 2004/0093167 A1 | 5/2004 | Braig et al. | |
| 2004/0111232 A1 | 6/2004 | Butler et al. | |
| 2004/0252300 A1 | 12/2004 | Slater | |
| 2005/0029453 A1 | 2/2005 | Allen et al. | |
| 2005/0057366 A1 | 3/2005 | Kadwell et al. | |
| 2005/0103989 A1 | 5/2005 | Watson et al. | |
| 2006/0044562 A1 | 3/2006 | Hagene et al. | |
| 2006/0183241 A1 | 8/2006 | Lehmann et al. | |
| 2006/0232675 A1 | 10/2006 | Chamberlain et al. | |
| 2006/0279632 A1 | 12/2006 | Anderson | |
| 2007/0018105 A1 | 1/2007 | Grimberg | |
| 2007/0075888 A1 | 4/2007 | Kelly et al. | |
| 2007/0108385 A1 | 5/2007 | Mantese et al. | |
| 2007/0170359 A1 | 7/2007 | Syllaios et al. | |
| 2007/0170363 A1 | 7/2007 | Schimert et al. | |
| 2008/0170140 A1 | 7/2008 | Silver et al. | |
| 2008/0204744 A1 | 8/2008 | Mir et al. | |
| 2008/0231719 A1 | 9/2008 | Benson et al. | |
| 2008/0251724 A1 | 10/2008 | Baliga et al. | |
| 2009/0015824 A1 | 1/2009 | Shubinsky et al. | |
| 2009/0252650 A1 | 10/2009 | Lakshmanan | |
| 2010/0162206 A1 | 6/2010 | Roth et al. | |
| 2010/0171866 A1 | 7/2010 | Brady et al. | |
| 2010/0211333 A1 | 8/2010 | Pruet et al. | |
| 2010/0309467 A1 | 12/2010 | Fox et al. | |
| 2011/0176577 A1 | 7/2011 | Bandara et al. | |
| 2011/0185048 A1 | 7/2011 | Yew et al. | |
| 2011/0261321 A1 | 10/2011 | Ramella-Roman et al. | |
| 2012/0273680 A1 | 11/2012 | Furry | |
| 2013/0181836 A1 | 7/2013 | Cardoso et al. | |
| 2013/0206990 A1 | 8/2013 | Hsu et al. | |
| 2013/0228887 A1 | 9/2013 | Wehner et al. | |
| 2013/0235256 A1 | 9/2013 | Kodama | |
| 2013/0250124 A1 | 9/2013 | Furry | |
| 2013/0307991 A1 | 11/2013 | Olsen et al. | |
| 2013/0321806 A1 | 12/2013 | Kester et al. | |
| 2013/0341509 A1 | 12/2013 | Nelson et al. | |
| 2013/0342680 A1 | 12/2013 | Zeng et al. | |
| 2014/0002639 A1 | 1/2014 | Cheben et al. | |
| 2014/0139643 A1 | 5/2014 | Högasten et al. | |
| 2014/0320843 A1 | 10/2014 | Streuber et al. | |
| 2015/0069239 A1 | 3/2015 | Kester et al. | |
| 2015/0136981 A1 | 5/2015 | Kester et al. | |
| 2015/0136982 A1 | 5/2015 | Kester et al. | |
| 2015/0138534 A1* | 5/2015 | Tidhar .................... F41G 3/147 356/51 | |
| 2015/0144770 A1 | 5/2015 | Choi | |
| 2015/0226613 A1 | 8/2015 | Bauer et al. | |
| 2015/0288894 A1 | 10/2015 | Geelen et al. | |
| 2015/0292948 A1 | 10/2015 | Goldring et al. | |
| 2015/0316473 A1 | 11/2015 | Kester et al. | |
| 2016/0037089 A1 | 2/2016 | Silny et al. | |
| 2016/0041095 A1 | 2/2016 | Rothberg et al. | |
| 2016/0097714 A1 | 4/2016 | Zeng et al. | |
| 2016/0238454 A1 | 8/2016 | Pillans | |
| 2016/0245698 A1 | 8/2016 | Pau et al. | |
| 2016/0313181 A1 | 10/2016 | Golub et al. | |
| 2016/0349228 A1 | 12/2016 | Kester et al. | |
| 2016/0356702 A1 | 12/2016 | Hinnrichs | |
| 2016/0380014 A1 | 12/2016 | Ganapathi et al. | |
| 2017/0026588 A1 | 1/2017 | Kester et al. | |
| 2017/0205290 A1 | 7/2017 | Kester et al. | |
| 2017/0234761 A1 | 8/2017 | Augusto | |
| 2017/0248517 A1 | 8/2017 | Scherer et al. | |
| 2017/0350758 A1 | 12/2017 | Kester et al. | |
| 2017/0356802 A1 | 12/2017 | Kester et al. | |
| 2018/0077363 A1 | 3/2018 | Kester et al. | |
| 2018/0188163 A1 | 7/2018 | Kester et al. | |

(56) References Cited

U.S. PATENT DOCUMENTS

2018/0191967 A1 7/2018 Kester
2019/0003984 A1 1/2019 Kester et al.

FOREIGN PATENT DOCUMENTS

| EP | 0 837 600 | 4/1998 |
|---|---|---|
| EP | 2 870 419 | 4/1998 |
| EP | 2 871 452 | 5/2015 |
| EP | 2 942 615 | 11/2015 |
| EP | 2 955 496 | 12/2015 |
| GB | 2518224 | 3/2015 |
| JP | 2013-128185 | 6/2013 |
| WO | WO 2004/097389 | 11/2004 |
| WO | WO 2007/008826 | 1/2007 |
| WO | WO 2009/094782 | 8/2009 |
| WO | WO 2010/053979 | 5/2010 |
| WO | WO 2012/078417 | 6/2012 |
| WO | WO 2012/082366 | 6/2012 |
| WO | WO 2013/173541 | 11/2013 |
| WO | WO 2015/108236 | 7/2015 |
| WO | WO 2017/201194 | 11/2017 |
| WO | WO 2018/075957 | 4/2018 |
| WO | WO 2018/075964 | 4/2018 |
| WO | WO 2018/156795 | 8/2018 |

OTHER PUBLICATIONS

U.S. Appl. No. 14/538,827, now U.S. Pat. No. 9,562,849, Divided-Aperture Infra-Red Spectral Imaging System, filed Nov. 12, 2014.
U.S. Appl. No. 15/418,532, 2017/0205290, Divided-Aperture Infra-Red Spectral Imaging System, filed Jan. 27, 2017.
U.S. Appl. No. 14/543692, now U.S. Pat. No. 9,625,318, Divided-Aperture Infra-Red Spectral Imaging System for Chemical Detection, filed Nov. 17, 2014.
U.S. Appl. No. 15/471,398, 2017/0356802, Divided-Aperture Infra-Red Spectral Imaging System for Chemical Detection, filed Mar. 28, 2017.
U.S. Appl. No. 14/539,899, now U.S. Pat. No. 9,599,508 Divided-Aperture Infra-Red Spectral Imaging System, filed Nov. 11, 2014.
U.S. Appl. No. 15/462,350, 2017/0350758, Divided-Aperture Infra-RED Spectral Imaging System, filed Mar. 17, 2017.
U.S. Appl. No. 14/700,791, now U.S. Pat. No. 9,756,263, Mobile Gas and Chemical Imaging Camera, filed Apr. 30, 2015.
U.S. Appl. No. 15/623,942, 2018/0077363, Mobile Gas and Chemical Imaging Camera, filed Jun. 15, 2017.
U.S. Appl. No. 14/700,567, 2017/0026588, Dual-Band Divided-Aperture Infra-Red Spectral Imaging System, filed Apr. 30, 2015.
U.S. Appl. No. 15/166,092, 2016/0349228, Hydrogen Sulfide Imaging System, filed May 26, 2016.
U.S. Appl. No. 15/789,811, 2018/0191967, Mobile Gas and Chemical Imaging Camera, filed Oct. 20, 2017.
U.S. Appl. No. 15/789,829, 2018/0188163, Gas Imaging System, filed Oct. 20, 2017.
U.S. Appl. No. 15/902,336, Systems and Methods for Monitoring Remote Installations, filed Feb. 22, 2018.
Cossel et al., "Analysis of Trace Impurities in Semiconductor Gas Via Cavity-Enhanced Direct Frequency Comb Spectroscopy", Applied Physics B, Sep. 2010, vol. 100, No. 4, pp. 917-924.
Sandsten et al., "Development of Infrared Spectroscopy Techniques for Environmental Monitoring", Doctoral Thesis, Aug. 2000, pp. 123.
Sandsten et al., "Real-Time Gas-Correlation Imaging Employing Thermal Background Radiation", Optics Express, Feb. 14, 2000, vol. 5, No. 4, pp. 92-103.
Official Communication received in U.S. Appl. No. 15/418,532, dated Jun. 23, 2017 in 7 pages.
Amendment as filed in U.S. Appl. No. 15/418.532, dated Nov. 22, 2017 in 8 pages.
Official Communication received in U.S. Appl. No. 15/418,532, dated Dec. 11, 2017 in 21 pages.
Notice of Allowance received in U.S. Appl. No. 15/418,532, dated Jun. 15, 2018 in 12 pages.
Corrected Notice of Allowance received in U.S. Appl. No. 15/418,532, dated Jul. 6, 2018 in 3 pages.
Notice of Allowance received in U.S. Appl. No. 14/571,398, dated Feb. 7, 2018 in 20 pages.
Official Communication received in U.S. Appl. No. 15/462,352, dated Sep. 28, 2017 in 6 pages.
Amendment as filed in U.S. Appl. No. 15/462,352, dated Feb. 28, 2018 in 5 pages.
Official Communication received in European Application No. 14192862.2, dated May 2, 2018 in 3 pages.
Preliminary Amendment as filed in U.S. Appl. No. 15/623,942, dated Dec. 7, 2017 in 6 pages.
Notice of Allowance received in U.S. Appl. No. 15/623,942, dated Jan. 24, 2018 in 22 pages.
Amendment as filed in U.S. Appl. No. 14/700,567 dated Dec. 13, 2017 in 12 pages.
Official Communication received in U.S. Appl. No. 14/700,567 dated Mar. 5. 2018 in 38 pages.
Official Communication received in U.S. Appl. No. 14/792,477 dated Jul. 19, 2017 in 20 pages.
Amendment as filed in U.S. Appl. No. 14/792,477 dated Jan. 18, 2018 in 10 pages.
Official Communication received in U.S. Appl. No. 15/166,092 dated May 15, 2018 in 30 pages.
Preliminary Amendment as filed in U.S. Appl. No. 15/789,811 dated Mar. 20, 2018 in 6 pages.
International Search Report in PCT Application No. PCT/US2017/057725 dated Feb. 14, 2018 in 14 pages.
Preliminary Amendment as filed in U.S. Appl. No. 15/789,829 dated Mar. 20, 2018 in 8 pages.
Official Communication received in U.S. Appl. No. 15/789,829 dated Jun. 5, 2018 in 16 pages.
International Search Report in PCT Application No. PCT/US2017/057712 dated Mar. 6, 2018 in 12 pages.
International Search Report in PCT Application No. PCT/US2018/019271 dated Jun. 27, 2018 in 15 pages.
Amendment after Allowance as filed in U.S. Appl. No. 15/418,532 dated Sep. 14, 2018 in 6 pages.
Notice of Allowance received in U.S. Appl. No. 15/418,532 dated Dec. 5, 2018 in 11 pages.
Notice of Allowance received in U.S. Appl. No. 14/571,398 dated Jul. 2, 2018 in 8 pages.
Notice of Allowance received in U.S. Appl. No. 14/571,398 dated Oct. 24, 2018 in 7 pages.
Notice of Allowance received in U.S. Appl. No. 15/462,352 dated Jul. 17, 2018 in 25 pages.
Notice to File Corrected Application Papers received in U.S. Appl. No. 15/462,352 dated Aug. 8, 2018 in 3 pages.
Response to Notice to File Corrected Application Papers filed in U.S. Appl. No. 15/462,352 dated Oct. 8, 2018 in 3 pages.
Notice of Allowance received in U.S. Appl. No. 15/462,352 dated Oct. 31, 2018 in 9 pages.
Official Communication received in European Application No. 13732285.5 dated Jul. 26, 2018 in 6 pages.
Notice of Allowance received in U.S. Appl. No. 15/623,942 dated May 24, 2018 in 23 pages.
Comments on Allowance filed in U.S. Appl. No. 15/623,942 dated Aug. 23, 2018 in 2 pages.
Amendment as filed in U.S. Appl. No. 14/700,567 dated Jul. 5, 2018 in 10 pages.
Office Action as filed in U.S. Appl. No. 14/700,567 dated Aug. 27, 2018 in 36 pages.
Amendment as filed in U.S. Appl. No. 15/166,092 dated Nov. 15, 2018 in 11 pages.
Official Communication received in U.S. Appl. No. 15/789,811 dated Jul. 27, 2018 in 22 pages.
Interview Summary recieved in U.S. Appl. No. 15/789,811 dated Nov. 20, 2018 in 3 pages.
Amendment as filed in U.S. Appl. No. 15/789,829 dated Dec. 4, 2018 in 9 pages.

(56) References Cited

OTHER PUBLICATIONS

Preliminary Amendment as filed in U.S. Appl. No. 15/902,336 dated Sep. 20, 2018 in 9 pages.
Weldon et al., "H2S and CO2 gas sensing using DFB laser diodes emitting at 1.57 μm", Sensors and Actuators B: Chemical, Oct. 1995, vol. 29, Issues 1-3, pp. 101-107.
Notice of Allowance received in U.S. Appl. No. 15/462,352 dated Feb. 12, 2019 in 9 pages.
Official Communication received in Canadian Application No. 2,873,989 dated Mar. 21, 2019 in 6 pages.
Extended European Search Report received in European Application No. EP 16804077.2 dated Jan. 8, 2019 in 8 pages.
Notice of Allowance received in U.S. Appl. No. 15/789,829 dated Feb. 25, 2019 in 28 pages.
Official Communication received in U.S. Appl. No. 16/185,399 dated Apr. 2, 2019 in 24 pages.
International Search Report in PCT Application No. PCT/US2018/059890 dated Jan. 23, 2019 in 10 pages.

\* cited by examiner

500

510

For each frame, calculate absorption spectra at each pixel from the difference between current frames radiance spectra and running mean of radiance spectra, $M^{(1)}(\lambda) - M^{(0)}(\lambda)$ $\alpha_C = [M^{(1)}(\lambda) - M^{(0)}(\lambda)] / [B(T_C) - M^{(0)}(\lambda)]$

520

Check whether calculated absorption spectra $\alpha_C$ matches spectra of a gas, $\sigma$, If no, go to next pixel If yes, calculate column density, $nl$ $nl = [M^{(1)}(\lambda) - M^{(0)}(\lambda) / \sigma[B(T_C) - M^{(0)}(\lambda)]$

530

(1) Average absorption over one or two spectral bands where gas absorption cross-section, $\sigma$, is significant; OR (2) Fit gas cross-section spectrum, $\sigma$, to the measured absorption spectrums, $\alpha_C$.

(Know which gases likely and hence which absorption cross-section spectra $\sigma$ to use. Can include such gases and absorption cross-section spectra in library.)

FIG. 5

GAS LEAK EMISSION QUANTIFICATION WITH A GAS CLOUD IMAGER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In particular, this application claims priority to U.S. Provisional Patent Applications 62/021,636, filed Jul. 7, 2014, 62/021,907, filed Jul. 8, 2014, and 62/083,131, filed Nov. 21, 2014, all of which are entitled "GAS LEAK EMISSION QUANTIFICATION WITH A GAS CLOUD IMAGER," and all of which are incorporated by reference herein in their entirety.

BACKGROUND

Field

This disclosure generally relates to systems and methods for gas cloud detection and gas leak emission quantification.

Description of the Related Art

There are a wide variety of systems that create, store, transfer, process, or otherwise involve gases. These include, but are not limited to, industrial systems, such as oil and gas drilling rigs and refineries. In such systems, there may be a risk of gas leaks. Such gases may include hydrocarbons (e.g., methane), ammonia, hydrogen sulfide, volatile organic compounds, and many, many others. Gas leaks can pose safety and/or environmental risks. They can also result in financial loss. It would therefore be advantageous to develop systems and methods for detecting gas leaks and quantifying gas leak emission.

SUMMARY

In some embodiments, an infrared (IR) imaging system for quantifying one or more parameters of a gas leak having a gaseous emission rate is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire multispectral optical data from the IR radiation received at the optical FPA unit and output gaseous emission rate data for a gaseous leak.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to determine absorption spectra data at a given pixel of a given frame by comparing spectral data for said pixel of said frame with spectral data from prior frames.

In some embodiments, a system for quantifying one or more parameters of a gas leak is disclosed, the system comprising: a communication subsystem for receiving multi-spectral optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said multispectral spectral optical data from said communication subsystem, wherein said data-processing unit is configured to process said multispectral optical data and output gaseous emission rate data from a gaseous leak.

In some embodiments, a system for quantifying one or more parameters of a gas leak is disclosed, the system comprising: a communication subsystem for receiving processed data derived from multi-spectral optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said processed data from said communication subsystem, wherein said data-processing unit is configured to further process said processed data and output gaseous emission rate data for a gaseous leak.

In some embodiments, a system for quantifying one or more parameters of a gas cloud is disclosed, the system comprising: a communication subsystem for receiving multi-spectral optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said multi-spectral optical data from said communication subsystem, wherein said data-processing unit is configured to determine absorption spectra data at a given pixel of a given frame from a comparison of spectral data for said pixel of said frame with spectral data from prior frames.

In some embodiments, a system for quantifying one or more parameters of a gas cloud is disclosed, the system comprising: a communication subsystem for receiving multi-spectral optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said multi-spectral optical data from said communication subsystem, wherein said data-processing unit is configured to compare spectral data for said pixel of said frame with spectral data from prior frames for the determination of absorption spectra data at a given pixel of a given frame.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said data-processing unit is configured to consider noise as a criteria for determining whether to include data for the given pixel for a particular prior frame with data from other prior frames for comparing spectral data for a pixel of a later frame with spectral data from prior frames for the determination of absorption spectra data for the given pixel of the later frame.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to determine gas emission by comparing data from a given frame with data from one or more prior frames.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to include an estimate of loss caused by a portion of said cloud being blown out of the field of view of the optical system.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said optical system and FPA unit together with said data-processing unit has a detection sensitivity for detecting absorption, and wherein said data-processing unit is configured to include an estimate of loss caused by a portion of said cloud having absorption less than the detection sensitivity.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to use noise as a criteria for determining whether to de-emphasize or exclude data for a particular frame.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to determine a quantity of gas using one or more specifications of the FPA unit, one or more specification of the optical system, distance of camera to the gas cloud, or combinations thereof.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said data-processing unit is configured to determine gas emission by comparing data from a given frame with data from one or more prior frames.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said data-processing unit is configured to include an estimate of loss caused by a portion of said cloud being blown out of the field of view of the optical system.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said optical system and FPA unit together with said data-processing unit has a detection sensitivity for detecting absorption, and wherein said data-processing unit is configured to include an estimate of loss caused by a portion of said cloud having absorption less than the detection sensitivity.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said data-processing unit is configured to use noise as a criteria for determining whether to de-emphasize or exclude data for a particular frame.

In some embodiments, a system for quantifying one or more parameters of a gas cloud is disclosed, the system comprising: a communication subsystem for receiving optical data produced by a camera including an optical focal plane array (FPA) unit, the camera having components defining at least two optical channels thereof, said at least two optical channels being spatially and spectrally different from one another, each of the at least two optical channels positioned to transfer IR radiation incident on the optical system towards the optical FPA, said multi-spectral optical data derived from the IR radiation received at the optical FPA; and a data-processing unit comprising one or more processors, said data-processing unit configured to acquire said optical data from said communication subsystem, wherein said data-processing unit is configured to determine a quantity of gas using one or more specifications of the FPA unit, one or more specification of the optical system, distance of camera to the gas cloud, or combinations thereof.

In some embodiments, an infrared (IR) imaging system for quantifying one or more parameters of a gas cloud is disclosed, the imaging system comprising: an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to include an estimate of atmospheric absorption between the gas cloud and the optical system.

In some embodiments, a method of analyzing a gas leak using a processor is disclosed, the method comprising: receiving a time series of data from a sensor, the data being capable of quantifying an absorption spectrum of a gas cloud located within a field of view of the sensor, the data comprising a frame for each time in the time series, each frame comprising optical signal values corresponding to different locations within the field of view for each of a plurality of spectral wavelengths of electromagnetic radiation; comparing a subsequent frame of data with at least one prior frame of data in the time series, analyzing at least one property of a gas cloud located within the field of view of the sensor based on the comparison between the subsequent frame of data and the at least one prior frame of data; and outputting an indicator of the at least one property of the gas cloud to a user interface.

In some embodiments, a method of analyzing the emission rate of a gas leak using a processor is disclosed, the method comprising: receiving a time series of data from a sensor, the data being capable of quantifying an absorption spectrum of a gas cloud located within a field of view of the sensor, the data comprising a frame for each time in the time series, each frame comprising optical signal values corresponding to different locations within the field of view for each of a plurality of spectral wavelengths of electromagnetic radiation; estimating the total amount of gas within the field of view of the sensor; temporally smoothing the estimate of the total amount of gas within the field of view; combining the temporally-smoothed estimate of the total amount of gas within the field of view with an estimate of the amount of gas that has exited the field of view; combining the temporally-smoothed estimate of the total amount of detected gas within the field of view of the sensor with an estimate of the amount of gas that has dropped below the sensitivity limit of the sensor; and outputting an indicator of the emission rate of the gas cloud to a user interface.

In some embodiments, a system for analyzing a gas leak is disclosed, the system comprising: at least one processor; and a non-transitory memory with instructions configured to cause the at least one processor to perform a method comprising: receiving a time series of data from a sensor, the data being capable of quantifying an absorption spectrum of a gas cloud located within a field of view of the sensor, the data comprising a frame for each time in the time series, each frame comprising optical signal values corresponding to different locations within the field of view for each of a plurality of spectral wavelengths of electromagnetic radiation; comparing a subsequent frame of data with at least one prior frame of data in the time series; analyzing at least one property of a gas cloud located within the field of view of the sensor based on the comparison between the subsequent frame of data and the at least one prior frame of data; and outputting an indicator of the at least one property of the gas cloud to a user interface.

In some embodiments, a system for analyzing the emission rate of a gas leak is disclosed, the system comprising: at least one processor; and a non-transitory memory with instructions configured to cause the at least one processor to perform a method comprising: receiving a time series of data from a sensor, the data being capable of quantifying an absorption spectrum of a gas cloud located within a field of view of the sensor, the data comprising a frame for each time in the time series, each frame comprising optical signal values corresponding to different locations within the field of view for each of a plurality of spectral wavelengths of electromagnetic radiation; estimating the total amount of gas within the field of view of the sensor; temporally smoothing the estimate of the total amount of gas within the field of view; combining the temporally-smoothed estimate of the total amount of gas within the field of view with an estimate of the amount of gas that has exited the field of view; combining the temporally-smoothed estimate of the total amount of detected gas within the field of view of the sensor with an estimate of the amount of gas that has dropped below the sensitivity limit of the sensor; and outputting an indicator of the emission rate of the gas cloud to a user interface.

BRIEF DESCRIPTION OF THE DRAWINGS

FIG. 5 is a flowchart of an example method for detecting a gas cloud.

FIG. 8 also illustrates the example scene as viewed from the gas cloud imager camera itself (right).

DETAILED DESCRIPTION

A. Gas Cloud Imagers

Figure 1:
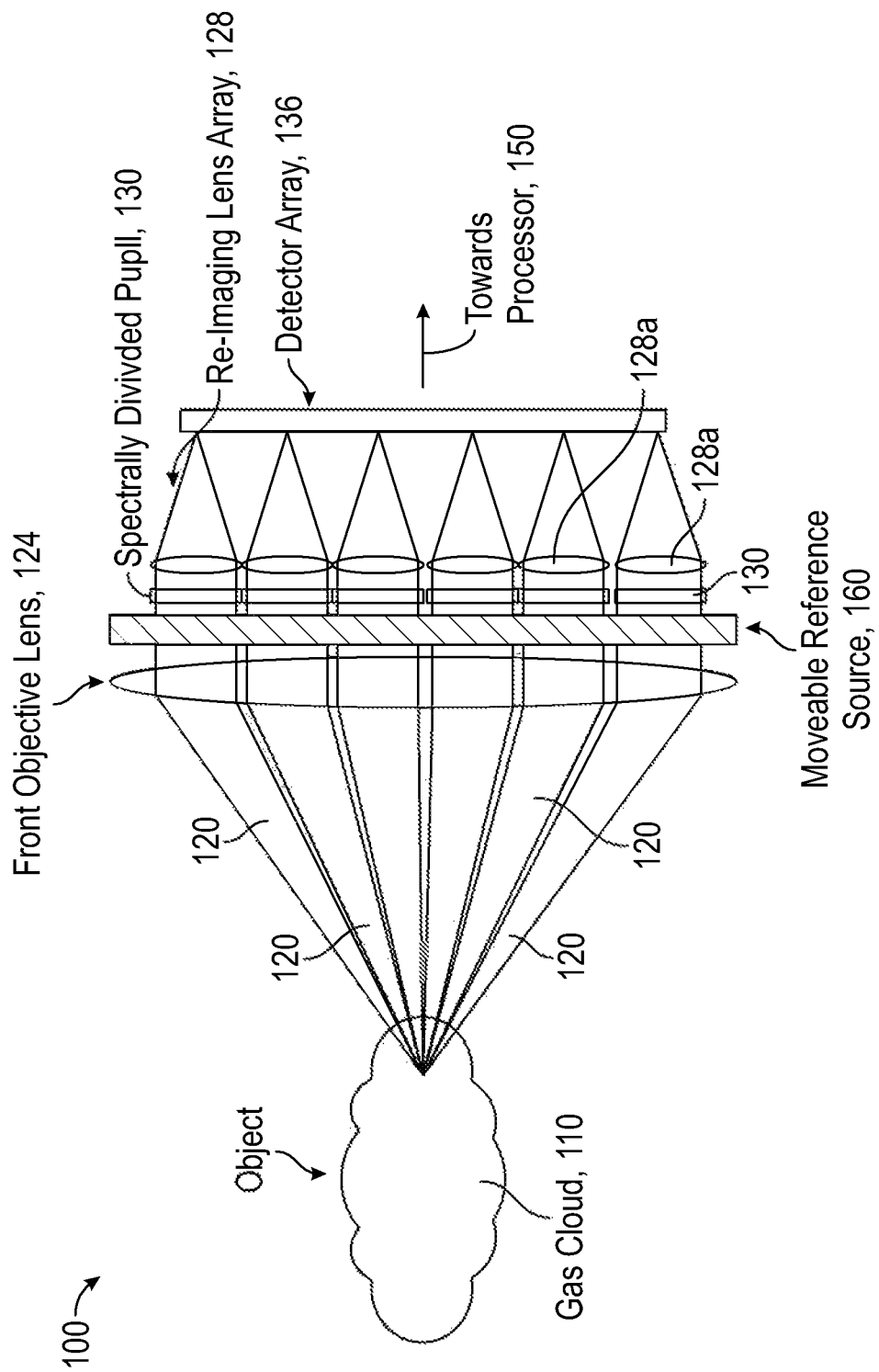
FIG. 1 provides a diagram schematically illustrating spatial and spectral division of incoming light by an embodiment of a divided aperture infrared spectral imager (DAISI) system that can image an object possessing IR spectral signature(s).

Various embodiments of gas cloud imager (GCI) instruments are disclosed in U.S. patent application Ser. No. 14/538,827, filed Nov. 12, 2014, and entitled "DIVIDED-APERTURE INFRA-RED SPECTRAL IMAGING SYSTEM," U.S. patent application Ser. No. 14/700,791, filed Apr. 30, 2015, and entitled "MOBIL GAS AND CHEMICAL IMAGING CAMERA," and in U.S. patent application Ser. No. 14/700,567, filed Apr. 30, 2015, and entitled "DUAL-BAND DIVIDED-APERTURE INFRA-RED SPECTRAL IMAGING SYSTEM." Each of the foregoing applications is hereby incorporated by reference herein in its entirety. The instruments disclosed in the foregoing applications are non-limiting examples of gas cloud imagers which may be used in conjunction with the algorithms disclosed herein.

By way of background, one type of gas cloud imager is a divided-aperture infrared spectral imaging (DAISI) system that is structured and adapted to provide identification of target chemical contents of the imaged scene. The system is based on spectrally-resolved imaging and can provide such identification with a single-shot (also referred to as a snapshot) comprising a plurality of images having different wavelength compositions that are obtained generally simultaneously.

Without any loss of generality, snapshot refers to a system in which most of the data elements that are collected are continuously viewing the light emitted from the scene. In contrast in scanning systems, at any given time only a minority of data elements are continuously viewing a scene, followed by a different set of data elements, and so on, until the full dataset is collected. Relatively fast operation can be achieved in a snapshot system because it does not need to use spectral or spatial scanning for the acquisition of infrared (IR) spectral signatures of the target chemical contents. Instead, IR detectors (such as, for example, infrared focal plane arrays or FPAs) associated with a plurality of different optical channels having different wavelength profiles can be used to form a spectral cube of imaging data. Although spectral data can be obtained from a single snapshot comprising multiple simultaneously-acquired images corresponding to different wavelength ranges, in various embodiments, multiple snap shots may be obtained. In various embodiments, these multiple snapshots can be averaged. Similarly, in certain embodiments multiple snap shots may be obtained and a portion of these can be selected and possibly averaged.

Also, in contrast to commonly used IR spectral imaging systems, the DAISI system does not require cooling (for example cryogenic cooling). Accordingly, it can advantageously use uncooled infrared detectors. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin.

Implementations disclosed herein provide several advantages over existing IR spectral imaging systems, most if not all of which may require FPAs that are highly sensitive and cooled in order to compensate, during the optical detection, for the reduction of the photon flux caused by spectrum-scanning operation. The highly sensitive and cooled FPA systems are expensive and require a great deal of maintenance. Since various embodiments disclosed herein are configured to operate in single-shot acquisition mode without spatial and/or spectral scanning, the instrument can receive photons from a plurality of points (e.g., every point) of the object substantially simultaneously, during the single reading. Accordingly, the embodiments of imaging system described herein can collect a substantially greater amount of optical power from the imaged scene (for example, an order of magnitude more photons) at any given moment in time especially in comparison with spatial and/or spectral scanning systems. Consequently, various embodiments of the imaging systems disclosed herein can be operated using uncooled detectors (for example, FPA unit including an array of microbolometers) that are less sensitive to photons in the IR but are well fit for continuous monitoring applications.

For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. Imaging systems including uncooled detectors can be capable of operating in extreme weather conditions, require less power, are capable of operation during day and night, and are less expensive. Some embodiments described herein can also be less susceptible to motion artifacts in comparison with spatially and/or spectrally scanning systems which can cause errors in either the spectral data, spatial data, or both.

FIG. 1 provides a diagram schematically illustrating spatial and spectral division of incoming light by an embodiment 100 of a divided aperture infrared spectral imager (DAISI) system that can image an object 110 possessing IR spectral signature(s). The system 100 includes a front objective lens 124, an array of optical filters 130, an array of reimaging lenses 128 and a detector array 136. In various embodiments, the detector array 136 can include a single FPA or an array of FPAs. Each detector in the detector array 136 can be disposed at the focus of each of the lenses in the array of reimaging lenses 128. In various embodiments, the detector array 136 can include a plurality of photo-sensitive devices. In some embodiments, the plurality of photo-sensitive devices may comprise a two-dimensional imaging sensor array that is sensitive to radiation having wavelengths between 1 µm and 20 µm (for example, in near infra-red wavelength range, mid infra-red wavelength range, or long infra-red wavelength range). In various embodiments, the plurality of photo-sensitive devices can include CCD or CMOS sensors, bolometers, microbolometers or other detectors that are sensitive to infra-red radiation. Without any loss of generality the detector array 136 can also be referred to herein as an imaging system or a camera.

An aperture of the system 100 associated with the front objective lens system 124 is spatially and spectrally divided by the combination of the array of optical filters 130 and the array of reimaging lenses 128. In various embodiments, the combination of the array of optical filters 130 and the array of reimaging lenses 128 can be considered to form a spectrally divided pupil that is disposed forward of the optical detector array 136. The spatial and spectral division of the aperture into distinct aperture portions forms a plurality of optical channels 120 along which light propagates. Various implementations of the system can include at least two spatially and spectrally different optical channels. For example, various implementations of the system can include at least three, at least four, at least five, at least six, at least seven, at least eight, at least nine, at least ten, at least eleven or at least twelve spatially and spectrally different optical channels. The number of spatially and spectrally different optical channels can be less than 50 in various implementations of the system. In various embodiments, the array 128 of re-imaging lenses 128a and the array of spectral filters 130 can respectively correspond to the distinct optical channels 120. The plurality of optical channels 120 can be spatially and/or spectrally distinct. The plurality of optical channels 120 can be formed in the object space and/or image space. The spatially and spectrally different optical channels can be separated angularly in space. The array of spectral filters 130 may additionally include a filter-holding aperture mask (comprising, for example, IR light-blocking materials such as ceramic, metal, or plastic).

Light from the object 110 (for example a cloud of gas), the optical properties of which in the IR are described by a unique absorption, reflection and/or emission spectrum, is received by the aperture of the system 100. This light propagates through each of the plurality of optical channels 120 and is further imaged onto the optical detector array 136. In various implementations, the detector array 136 can include at least one FPA. In various embodiments, each of the re-imaging lenses 128a can be spatially aligned with a respectively-corresponding spectral region. In the illustrated implementation, each filter element from the array of spectral filters 130 corresponds to a different spectral region. Each re-imaging lens 128a and the corresponding filter element of the array of spectral filter 130 can coincide with (or form) a portion of the divided aperture and therefore with respectively-corresponding spatial channel 120. Accordingly, in various embodiments an imaging lens 128a and a corresponding spectral filter can be disposed in the optical path of one of the plurality of optical channels 120. Radiation from the object 110 propagating through each of the plurality of optical channels 120 travels along the optical path of each re-imaging lens 128a and the corresponding filter element of the array of spectral filter 130 and is incident on the detector array (e.g., FPA component) 136 to form a single image (e.g., sub-image) of the object 110.

The image formed by the detector array 136 generally includes a plurality of sub-images formed by each of the optical channels 120. Each of the plurality of sub-images can provide different spatial and spectral information of the object 110. The different spatial information results from some parallax because of the different spatial locations of the smaller apertures of the divided aperture. In various embodiments, adjacent sub-images can be characterized by close or substantially equal spectral signatures.

The detector array (e.g., FPA component) 136 is further operably connected with a data-processing unit that includes a processor 150 (not shown). The processor can comprise processing electronics. The data-processing unit can be located remotely from the detector array 136. For example, in some implementations, the data-processing unit can be located at a distance of about 10-3000 feet from the detector array 136. As another example, in some other implementations, the data-processing unit can be located at a distance less than about 10 feet from the detector array 136 or greater than about 3000 feet. The data-processing unit can be connected to the detector array by a wired or a wireless communication link. The detector array (e.g., FPA component) 136 and/or the data-processing unit can be operably connected with a display device.

The processor or processing electronics 150 can be programmed to aggregate the data acquired with the system 100 into a spectral data cube. The data cube represents, in spatial (x, y) and spectral (λ) coordinates, an overall spectral image of the object 110 within the spectral region defined by the combination of the filter elements in the array of spectral filters 130. Additionally, in various embodiments, the processor or processing electronics 150 may be programmed to determine the unique absorption characteristic of the object 110. Also, the processor 150 can, alternatively or in addition, map the overall image data cube into a cube of data representing, for example, spatial distribution of concentrations, c, of targeted chemical components within the field of view associated with the object 110.

The Processor

Various implementations of the embodiment 100 can include an optional moveable temperature-controlled reference source 160 including, for example, a shutter system comprising one or more reference shutters maintained at different temperatures. The reference source 160 can include a heater, a cooler or a temperature-controlled element configured to maintain the reference source 160 at a desired temperature. For example, in various implementations, the embodiment 100 can include two reference shutters maintained at different temperatures. In various implementations including more than one reference shutter, some of the shutters may not be temperature controlled. The reference source 160 is removably and, in one implementation, periodically inserted into an optical path of light traversing the system 100 from the object 110 to the detector array (e.g., FPA component) 136 along at least one of the channels 120. The removable reference source 160 thus can block such optical path. Moreover, this reference source 160 can provide a reference IR spectrum to recalibrate various components including the detector array 136 of the system 100 in real time.

In the embodiment 100 illustrated in FIG. 1, the front objective lens system 124 is shown to include a single front objective lens positioned to establish a common field-of-view (FOV) for the reimaging lenses 128a and to define an aperture stop for the whole system. In this specific case, the aperture stop substantially spatially coincides with and/or is about the same size or slightly larger, as the plurality of smaller limiting apertures corresponding to different optical channels 120. As a result, the positions for spectral filters of the different optical channels 120 coincide with the position of the aperture stop of the whole system, which in this example is shown as a surface between the lens system 124 and the array 128 of the reimaging lenses 128a. In various implementations, the lens system 124 can be an objective lens 124. However, the objective lens 124 is optional and various embodiments of the system 100 need not include the objective lens 124. In various embodiments, the objective lens 124 can slightly shift the images obtained by the different detectors in the array 136 spatially along a direction perpendicular to optical axis of the lens 124, thus the functionality of the system 100 is not necessarily compromised when the objective lens 124 is not included. Generally, however, the field apertures corresponding to different optical channels may be located in the same or different planes. These field apertures may be defined by the aperture of the reimaging lens 128a and/or filters in the divided aperture 130 in certain implementations. In one implementation, the field apertures corresponding to different optical channels can be located in different planes and the different planes can be optical conjugates of one another. Similarly, while all of the filter elements in the array of spectral filters 130 of the embodiment 100 are shown to lie in one plane, generally different filter elements of the array of spectral filter 130 can be disposed in different planes. For example, different filter elements of the array of spectral filters 130 can be disposed in different planes that are optically conjugate to one another. However, in other embodiments, the different filter elements can be disposed in non-conjugate planes.

Figure 2:
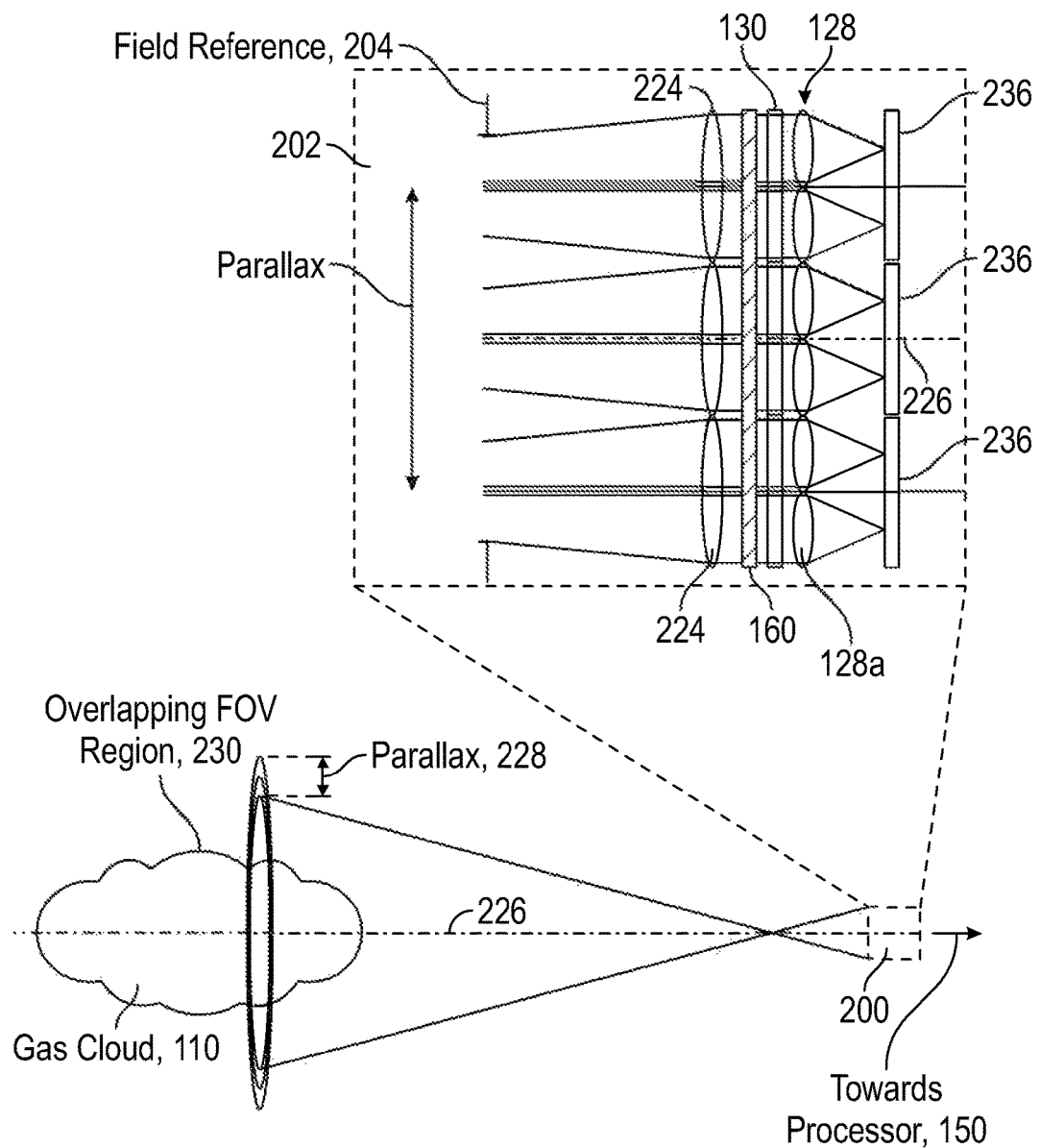
FIG. 2 illustrates another embodiment of a spectral imager system.

In various implementations, the front objective lens 124 need not be a single optical element, but instead can include a plurality of lenses 224 as shown in an embodiment 200 of the DAISI imaging system in FIG. 2. These lenses 224 are configured to divide an incoming optical wavefront from the object 110. For example, the array of front objective lenses 224 can be disposed so as to receive an IR wavefront emitted by the object that is directed toward the DAISI system. The plurality of front objective lenses 224 divide the wavefront spatially into non-overlapping sections. FIG. 2 shows three objective lenses 224 in a front optical portion of the optical system contributing to the spatial division of the aperture of the system in this example. The plurality of objective lenses 224, however, can be configured as a two-dimensional (2D) array of lenses.

FIG. 2 presents a general view of the imaging system 200 and the resultant field of view of the imaging system 200. An exploded view 202 of the imaging system 200 is also depicted in greater detail in a figure inset of FIG. 2. As illustrated in the detailed view 202, the embodiment of the imaging system 200 includes a field reference 204 at the front end of the system. The field reference 204 can be used to truncate the field of view. The configuration illustrated in FIG. 2 has an operational advantage over embodiment 100 of FIG. 1 in that the overall size and/or weight and/or cost of manufacture of the embodiment 200 can be greatly reduced because the objective lens is smaller. Each pair of the lenses in the array 224 and the array 128 is associated with a field of view (FOV). Each pair of lenses in the array 224 and the array 128 receives light from the object from a different angle. While the lenses 224 are shown to be disposed substantially in the same plane, optionally different objective lenses in the array of front objective lenses 224 can be disposed in more than one plane. For example, some of the individual lenses 224 can be displaced with respect to some other individual lenses 224 along the axis 226 (not shown) and/or have different focal lengths as compared to some other lenses 224. As discussed below, the field reference 204 can be useful in calibrating the multiple detectors 236.

In one implementation, the front objective lens system such as the array of lenses 224 is configured as an array of lenses integrated or molded in association with a monolithic substrate. Such an arrangement can reduce the costs and complexity otherwise accompanying the optical adjustment of individual lenses within the system. An individual lens 224 can optionally include a lens with varying magnification. As one example, a pair of thin and large diameter Alvarez plates can be used in at least a portion of the front objective lens system. Without any loss of generality, the Alvarez plates can produce a change in focal length when translated orthogonally with respect to the optical beam.

Referring to FIG. 1, the detector array 136 (e.g., FPA component) configured to receive the optical data representing spectral signature(s) of the imaged object 110 can be configured as a single imaging array (e.g., FPA) 136. This single array may be adapted to acquire more than one image (formed by more than one optical channel 120) simultaneously. Alternatively, the detector array 136 may include a FPA unit. In various implementations, the FPA unit can include a plurality of optical FPAs. At least one of these plurality of FPAs can be configured to acquire more than one spectrally distinct image of the imaged object. For example, as shown in the embodiment 200 of FIG. 2, in various embodiments, the number of FPAs included in the FPA unit may correspond to the number of the front objective lenses 224. In the embodiment 200 of FIG. 2, for example, three FPAs 236 are provided corresponding to the three objective lenses 224. In one implementation of the system, the FPA unit can include an array of microbolometers. The use of multiple microbolometers advantageously allows for an inexpensive way to increase the total number of detection elements (i.e. pixels) for recording of the three-dimensional data cube in a single acquisition event (i.e. one snapshot). In various embodiments, an array of microbolometers more efficiently utilizes the detector pixels of the array of FPAs (e.g., each FPA) as the number of unused pixels is reduced, minimized and/or eliminated between the images that may exist when using a single microbolometer. The optical filters, used in various implementations of the system, that provide spectrally-distinct IR image (e.g., sub-image) of the object can employ absorption filters, interference filters, and Fabry-Perot etalon based filters, to name just a few. When interference filters are used, the image acquisition through an individual imaging channel defined by an individual re-imaging lens (such as a lens 128a of FIGS. 1 and 2) may be carried out in a single spectral bandwidth or multiple spectral bandwidths.

The optical filtering configuration of various embodiments disclosed herein may advantageously use a bandpass filter having a specified spectral band. The filters may be placed in front of the optical FPA (or generally, between the optical FPA and the object). In implementations of the system that include microbolometers, the predominant contribution to noise associated with image acquisition can be attributed to detector noise. To compensate and/or reduce the noise, various embodiments disclosed herein utilize spectrally-multiplexed filters. In various implementations, the spectrally-multiplexed filters can comprise a plurality of long pass (LP) filters, a plurality of band pass filters and any combinations thereof. A LP filter generally attenuates shorter wavelengths and transmits (passes) longer wavelengths (e.g., over the active range of the target IR portion of the spectrum). In various embodiments, short-wavelength-pass (SP) filters, may also be used. A SP filter generally attenuates longer wavelengths and transmits (passes) shorter wavelengths (e.g., over the active range of the target IR portion of the spectrum). At least in part due to the snap-shot/non-scanning mode of operation, embodiments of the imaging system described herein can use less sensitive microbolometers without compromising the SNR. The use of microbolometers, as detector-noise-limited devices, in turn not only benefits from the use of spectrally multiplexed filters, but also does not require cooling of the imaging system during normal operation.

As discussed above, various embodiments may optionally, and in addition to a temperature-controlled reference unit (for example temperature controlled shutters such as shutter 160), employ a field reference component, or an array of field reference components (e.g., filed reference apertures), to enable dynamic calibration. Such dynamic calibration can be used for spectral acquisition of one or more or every data cube. Such dynamic calibration can also be used for a spectrally-neutral camera-to-camera combination to enable dynamic compensation of parallax artifacts. The use of the temperature-controlled reference unit (for example, temperature-controlled shutter system 160) and field-reference component(s) facilitates maintenance of proper calibration of each of the FPAs individually and the entire FPA unit as a whole.

In particular, and in further reference to FIGS. 1 and 2, the temperature-controlled unit generally employs a system having first and second temperature zones maintained at first and second different temperatures. For example, shutter system of each of the embodiments 100 and 200 can employ not one but at least two temperature-controlled shutters that are substantially parallel to one another and transverse to the general optical axis 226 of the embodiment(s) 100 and 200. Two shutters at two different temperatures may be employed to provide more information for calibration; for example, the absolute value of the difference between FPAs at one temperature as well as the change in that difference with temperature change can be recorded. As discussed above, only one of the two shutters can be temperature controlled in various implementations while the other is not. In various implementations, multiple shutters can be employed to create a known reference temperature difference perceived by the FPA. This reference temperature difference is provided by the IR radiation emitted by the multiple shutters when they are positioned to block the radiation from the object 110. As a result, not only the offset values corresponding to each of the individual FPAs pixels can be adjusted but also the gain values of these FPAs. In an alternative embodiment, the system having first and second temperature zones may include a single or multi-portion piece. This single or multi-portion piece may comprise for example a plate. This piece may be mechanically-movable across the optical axis with the use of appropriate guides and having a first portion at a first temperature and a second portion at a second temperature.

Various implementations of the DAISI system can include a variety of temperature calibration elements to facilitate dynamic calibration of the FPAs. The temperature calibration elements can include mirrors as well as reference sources. The use of optically-filtered FPAs in various embodiments of the system described herein can provide a system with higher number of pixels. For example, embodiments including a single large format microbolometer FPA array can provide a system with large number of pixels. Various embodiments of the systems described herein can also offer a high optical throughput for a substantially low number of optical channels. For example, the systems described herein can provide a high optical throughput for a number of optical channels between 4 and 50. By having a lower number of optical channels (e.g., between 4 and 50 optical channels), the systems described herein have wider spectral bins which allows the signals acquired within each spectral bin to have a greater integrated intensity.

B. Gas Leak Quantification with a Gas Cloud Imager

The idea of using passive infrared absorption spectroscopy to detect and analyze gas clouds is an idea that has been pursued for decades, but whose implementation in an autonomous setting has remained out of reach. The primary difficulty with adapting these instruments to industrial use has been their low data rate—gas clouds are dynamic phenomena and require video analytics to properly detect them. As discussed herein, recently, advanced spectral imaging instruments have become available that improve light collection capacity and allow for video-rate imaging. Even with these new instruments, however, existing computational methods are incapable of performing autonomous operation, as they require supervision from an operator in order to function. In the discussion below, we provide alternative methods for detection and quantification of gas clouds that allow fully autonomous operation.

1. Conventional Measurement Model

Figure 3:
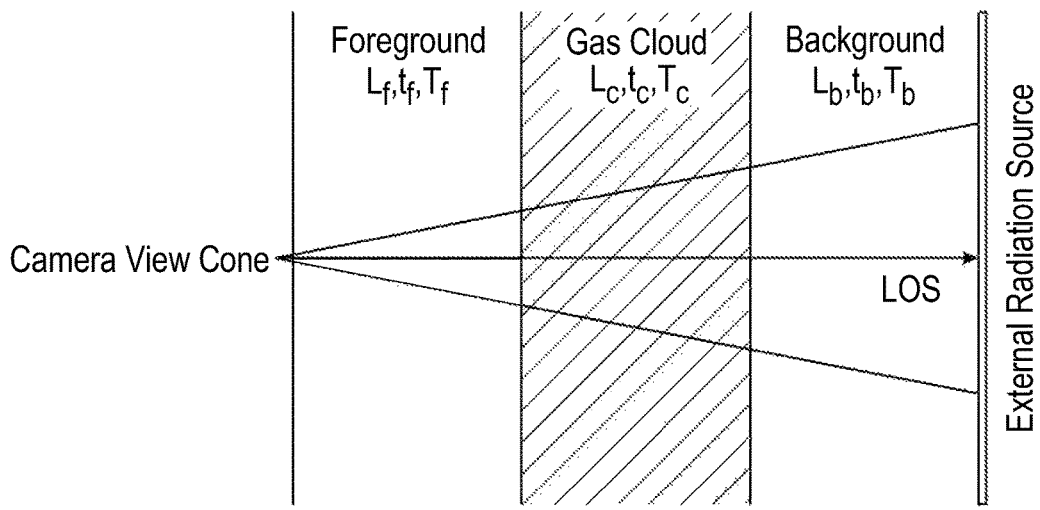
FIG. 3 illustrates an example of the measurement geometry for a gas cloud imager (GCI).

For a passive infrared sensor, the typical gas cloud measurement model is a three-layer radiative transfer system, in which the ray path is divided into three regions: (1) a layer of atmosphere between the sensor and the gas cloud, (2) a layer containing one or more of the target gases, and (3) an atmosphere behind the gas. Layer (3) is followed by a radiation source, which may either be an opaque surface or the sky itself. In the following discussion, we use the following definitions:

$L_f$, $L_b$, $L_s$: radiances originating from foreground, background, and source layers $\tau_f$, $\tau_b$, $\tau_c$: transmission of foreground, background, and cloud layers $T_f$, $T_b$, $T_c$: temperatures of foreground, background, and cloud layers $M^{(0)}$, $M^{(1)}$: at-sensor radiance in the absence (0) or presence (1) of the cloud $\sigma_m$: absorption cross-section of target gas m $\eta_m$: concentration of target gas m l: path length through the gas cloud FIG. 3 illustrates an example of the measurement geometry for a gas cloud imager (GCI). As just discussed, the field of view of each pixel (with line of sight indicated by "LOS") is divided into three layers and an external source.

A spectral imager measures the at-sensor radiance given by the line integral of the light extending from the source, through each of the three layers of the system (see FIG. 3). When no gas cloud is present, radiative transfer of a ray along the line of sight gives $$M^{(0)} = L_f + \tau_f L_b + \tau_f T_b L_s.$$

When a gas cloud is present, this becomes $$M^{(1)} = L_f + \tau_f (1-\tau_c) B(T_c) + \tau_f \tau_c L_b + \tau_f \tau_c \tau_b L_s.$$

Subtracting $M^{(0)}$ from $M^{(1)}$ gives the radiance difference in the presence of the target gas cloud:

$$\Delta M \equiv M^{(1)} - M^{(0)} = -\tau_f (1-\tau_c)[L_b + \tau_b L_s - B(T_c)], \quad (1)$$

where $\Delta L$, the term $[L_b + \tau_b L_s - B(T_c)]$, is the "thermal radiance contrast," the sign of which indicates whether the cloud is observed in emission ($\Delta L < 0$) or absorption ($\Delta L > 0$). When the background may be approximated as a homogeneous layer at thermal equilibrium, we can further write that $L_b = (1-\tau_b) B(T_b)$. Note that all of these quantities have an implicit spectral dependence (i.e. $M^{(0)} \equiv M^{(0)}(\lambda)$ etc.).

Thus, if we measure the change in at-sensor radiance, $\Delta M$, and we can estimate the thermal radiance contrast $\Delta L$ and foreground transmission $\tau_f$, then we can obtain the gas cloud transmission $\tau_c$ as $$1 - \tau_c = -\Delta M / (\tau_f \Delta L) \quad (2)$$

When the gas concentration is low, the transmission can be modeled with a linearized version of the Beer-Lambert equation obtained by Taylor expansion:

$$1 - \tau_c = 1 - e^{\alpha_c} = \alpha_c + \frac{1}{2!}\alpha_c^2 + \ldots \approx \alpha_c \quad (3)$$

for absorbance $\alpha_c$. For a single gas, the absorbance can be written in terms of the absorption cross-section $\sigma$, the number density (or "concentration") n, and the path length l through the layer as $\alpha_c = \sigma n l$. Using (3) to substitute this into (2) gives $$nl \approx \frac{\Delta M}{\tau_f \sigma \Delta L}, \quad (4)$$

where the left hand side represents the quantity we want to know—the concentration×path length, or "column density."

In order to use (4), the approach taken in the existing literature is generally the following. First we either take $\tau_f = 1$; $\tau_b = 1$ or the operator provides independent estimates of the transmission spectra $\tau_f(\lambda)$ and $\tau_b(\lambda)$. The gas absorption cross-section spectrum $\sigma(\lambda)$ is easily obtained from a spectral library. The remaining unknowns are $T_b$, $L_s$, and $T_c$. The temperature of the gas cloud $T_c$ and the atmosphere behind it $T_b$ are often taken as being the same and estimated by the operator using an independent measurement of the air temperature. Finally, the source radiance $L_s$ is generally taken to be either a greybody (if the background is an opaque surface) or is estimated from radiative transfer modelling software, such as MODTRAN.

2. General Approach for Autonomous Operation

The computational approach proceeds as follows:

1. Rather that attempting to estimate the absolute quantity of the gas present in a scene, we attempt to estimate the change in the gas, relative to either an initial time or to a running average. This allows for a simplification of the measurement model, so that many of the unknown quantities no longer need to be estimated.

2. We have found that using a running average of the scene is important not only for gas detection (as in the step above) but also for discriminating moving objects (such as people, cars, birds, etc.) from potential gas clouds. Some care must be taken when calculating the running mean, however, in order to prevent gas clouds and moving objects from "burning in" their signal into the running mean.

3. From the difference between the current frame's radiance spectrum to that of the running mean, we can calculate the absorption spectrum at each pixel. From the absorption spectrum, we can estimate the gas column density by either averaging the absorption over a few selected bands or by fitting the cross-section spectrum to the measured absorption value.

4. If the distance to the gas cloud is known or can be estimated by the camera, then we can scale the detected gas column density (ppm·m units) into absolute quantity units (kg). Summing over all pixels in the scene therefore gives an estimate of the total gas quantity (in kg) within the cloud at a given time.

5. In order to estimate total emission, one cannot simply use the value obtained in the previous step (the total gas quantity at a single snapshot in time), since the same cloud can be obtained by either a slow leak into an environment with little wind, or a fast leak into an environment with strong wind conditions. Rather, total emission is better measured by first estimating the emission rate over a period of time, and then integrating over that time period to get the total gas emission.

6. For the gas emission rate, we start by taking a running average of the total detected gas in a scene. We then use a heuristic method for estimating how much of the gas cloud in the previous frame we expect to have lost measurement sensitivity to, and add that value to the current frame's total gas volume. Finally, if we have knowledge of the wind direction and speed relative to the camera's pointing direction, then we can easily estimate how much gas is left in the field of view in the previous frame. This value is also added to the current frame's total gas volume. If we take this "augmented" estimate of the current frame's total gas volume, any changes in this value (if positive) indicate emission.

7. If we monitor a gas cloud over a period of time and sum the emission rate over the monitor period, we have an estimate for the total gas quantity emitted.

3. New Measurement Model

As shown above, the conventional method uses a number of steps in which an operator must manually specify quantities in order for the computation to proceed. This type of method cannot be performed autonomously under conditions of changing weather, temperature, etc. It also makes the assumption that the source (if an opaque surface) is a greybody—an assumption that we see violated in much of our own testing. We develop an alternative model that does not require these assumptions for the measurement to proceed. Rather than attempting to measure the absolute gas absorption spectrum $\Delta M(\lambda)$, we instead measure only the change in the spectrum, with respect to either an initial measurement, or with respect to a running average of the scene. This allows us to drop all of the background layer from the measurement model, so that the no-gas at-sensor radiance, with-gas at-sensor radiance, and their difference are now $$M^{(0)} = L_f + \tau_f L_s$$

$$M^{(1)} = L_f \tau_f (1-\tau_c) B(T_c) + \tau_f \tau_c L_s$$

$$\Delta M = M^{(1)} - M^{(0)} = \tau_f (1-\tau_c)[B(T_c) - L_s],$$

If we ignore the path absorption in the foreground (i.e. set $\tau_f = 1$), then the at-sensor radiance without gas is now equal to the source radiance ($M^{(0)} \approx L_s$), so that solving for the gas transmission gives $$1 - \tau_c \approx \alpha_c = \frac{M^{(1)} - M^{(0)}}{B(T_c) - M^{(0)}}, \quad (5)$$

Here we can interpret the quantity $M^{(0)}(\lambda)$ as being either the at-sensor radiance spectrum measured at an initial time, or as a running mean of the at-sensor radiance, so that what we choose to measure will be fluctuations about a mean value. Since gas clouds on this scale are dynamic and fast-moving phenomena, this method still produces excellent gas cloud detection, as we will show below. Finally, for estimation of the gas column density nl from measurements, we use $$nl = \frac{M^{(1)} - M^{(0)}}{\sigma[B(T_c) - M^{(0)}]}, \quad (6)$$

4. Calculating a Running Average of a Scene

Figure 4:
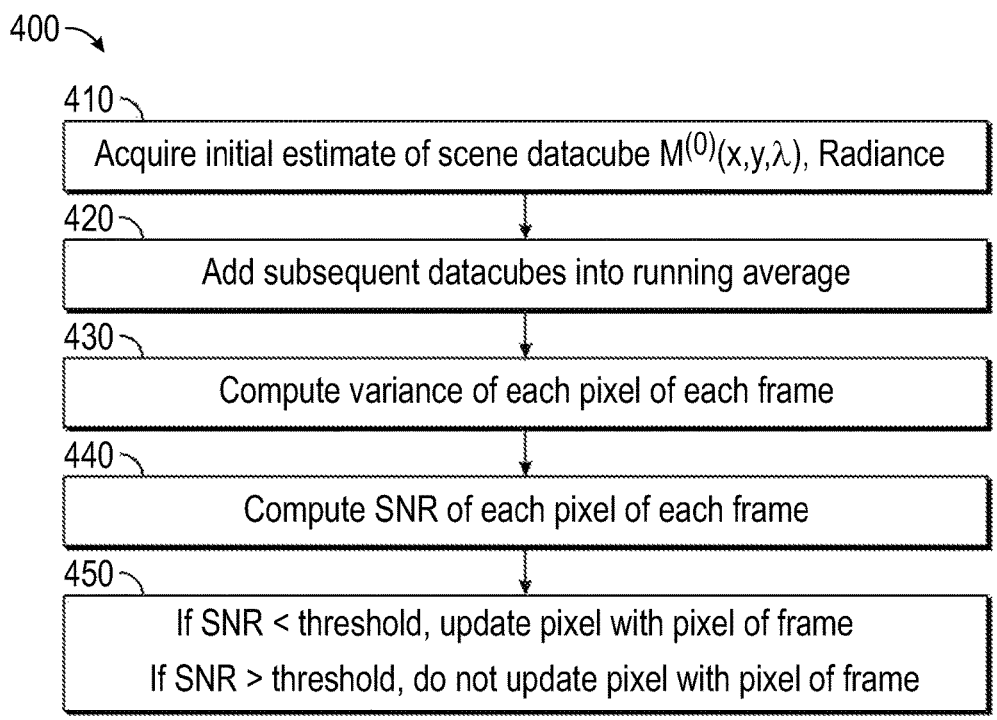
FIG. 4 is a flowchart of an example method for calculating a running average of a scene spectral distribution.

Experimentally, we have found that using a running average of the scene spectral distribution $\langle M(x, y, \lambda, t) \rangle_t$ provides much better results than using the scene spectral distribution at an initial time $M(x, y, \lambda, t_0)$ From here on, we will refer to the scene spectral distribution as the scene "datacube" Calculating the running average comprises several steps, as illustrated in FIG. 4, which is a flowchart of an example method 400 for calculating a running average of the scene spectral distribution:

1. First, as illustrated in block 410, the system needs to acquire an initial estimate of the scene reference datacube $M^{(0)}(x,y,\lambda)$. For this we simply collect a sequence of datacubes of the scene and average them together. Until a reliable initial estimate is formed, the system cannot attempt gas cloud detection, since the results are no more reliable than the reference datacube is.

2. After the initial estimate of $M^{(0)}(x,y,\lambda)$ is formed, as illustrated in block 420, we can add subsequent datacubes into our running average using the well-known updating algorithm (given here in pseudocode):

$$\Delta x = x_i - \bar{x} \quad (a)$$

$$x + = \Delta x / i \quad (b)$$

where x is the quantity to average (such as the scene datacube), $x_{mean}$ is its running mean, and i is the frame counter (i.e. if the current frame is the 15th, then i=14, since the counter starts at zero.

3. While the simple running average improves detection, over what can be achieved with a simple initial estimate that is not updated, problems can occur as a result of moving objects in the scene. For example, if a car drives through the scene, the radiance of the car is likely to be quite different from that of the radiance of the scene behind the car (and now being blocked by the car). Since the car will soon exit that region of the scene, leaving the original background exposed once more, it will degrade performance of the system if it were allowed to change the reference datacube. Since moving objects generally cause large signal changes, a powerful method to mitigate their effect on the reference datacube is to allow the moving average update to occur only if a given pixel experiences a small signal change and not a large one. Empirically, what we have found to work best is to place a threshold on the estimated SNR of a pixel: if a pixel's estimated SNR value is above 2.5, do not use the current frame to update that pixel in the reference datacube. If a pixel's estimated SNR is below 2.5, then go ahead and allow it to be updated.

4. This method therefore uses a running estimate of the SNR, which is calculated as follows. Along with the algorithm that continuously updates the reference datacube with each new frame, we also calculate and continuously update an estimated variance with each new frame, as illustrated in blocks 430 and 440. The above algorithm therefore becomes $$\Delta x = x_i - \bar{x} \quad (a)$$

$$x_{mean} + = \Delta x / i \quad (b)$$

$$m_2 + = \Delta x * (x - x_{mean}) \quad (c)$$

$$\mathrm{var}_x = m_2 / (i-1) \quad (d)$$

$$SNR_x = (x - x_{mean}) / \sqrt{\mathrm{var}_x} \quad (e)$$

where $\mathrm{var}_x$ is the estimated variance for the pixel at the current frame, $\sqrt{\mathrm{var}_x}$ is the corresponding estimated standard deviation. Thus, as illustrated in block 450, for any pixel whose SNR value is above the threshold (we typically use 2.5), the previous frame's value at that pixel is the one used in the "updated" reference datacube. For any pixel whose SNR is at or below the threshold, the above algorithm applies the update (i.e. it uses the new value for $x_{mean}$ rather than the previous frame's $x_{mean}$ for the pixel's value in the reference datacube).

5. Calculating the Absorption, Gas Column Density, and Absolute Quantity of Gas

FIG. 5 is a flowchart of an example method 500 for detecting a gas cloud. For passive absorption spectroscopy, measuring the absorption by a gas requires knowing the quantity of light reaching the sensor both with and without the gas. For autonomous measurement, since we can never ensure that we have available a measurement in which no gas is present, we instead attempt to measure only the changes in the gas concentration, rather than the absolute concentration values, as illustrated in block 510. Thus, the absorption spectrum at a pixel is given by (5), where $M^{(0)}$ represents the reference datacube, $M^{(1)}$ is the datacube obtained in the current frame, $B(T_c)$ is the Planck blackbody spectrum at temperature $T_c$, and $T_c$ is the gas cloud temperature. As shown in block 520, from the absorption spectrum at a pixel, we can perform spectral matching to estimate the probability that the absorption indicates presence of a gas. If the gas detection algorithm indicates that there is a high probability of there being a gas cloud at a given pixel, then we can go to the next step and calculate the gas column density at the pixel.

As shown in block 530, there are two basic techniques for estimating the gas column density. The first technique is to average the absorption over one or more spectral bands in which the gas absorption cross-section is significant (i.e. not close to zero). A second technique is to use a statistical method to fit the gas cross-section spectrum to the measured absorption spectrum. Both of these techniques work, with the former requiring less computation, and the latter being more accurate but also more in need of regularization. Once we have the column density (in, say, units of ppm·m), the next step is to convert the measurement units to an absolute quantity. In order to convert a measurement in ppm·m units to one in ppm·m³ units, we need only calculate the effective area of a pixel projected onto the gas cloud.

Figure 6:
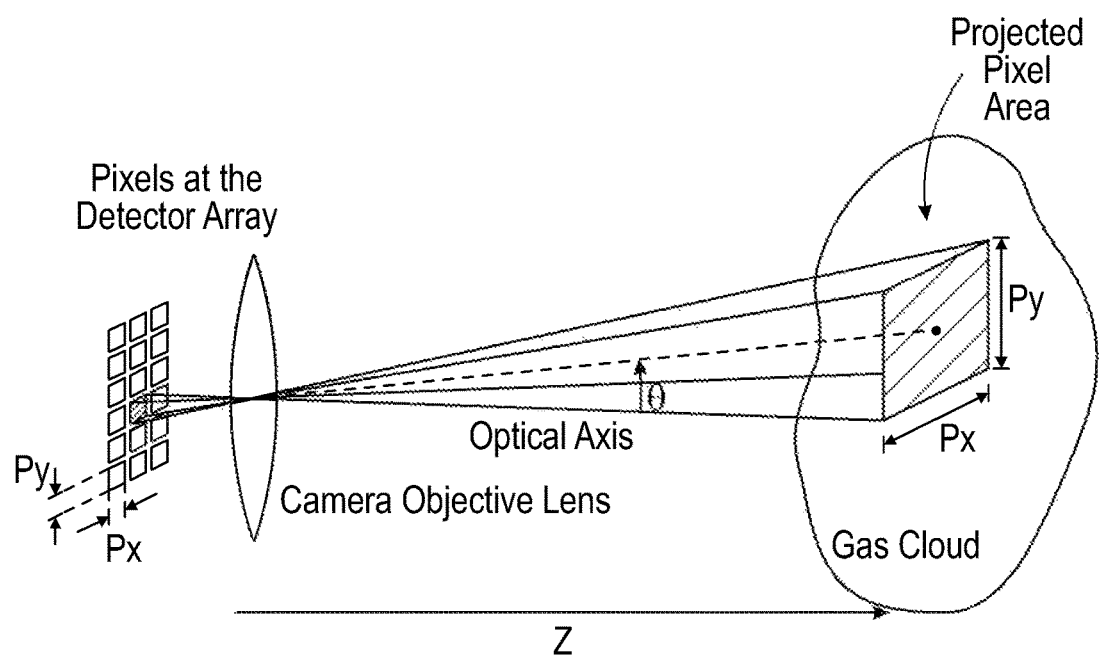
FIG. 6 illustrates a gas cloud imager detector pixel projected to the location of the gas cloud.

FIG. 6 illustrates a gas cloud imager detector pixel projected to the location of the gas cloud. Using the known dimensions of the detector array pixels ($p_x$, $p_y$), the focal length f of the objective lens, and the gas cloud distance z, we can calculate the projected dimension of the pixel at the plane of the gas cloud as $$\frac{P_x}{z} = \frac{p_x}{f} \rightarrow P_x = p_x z / f.$$

Since most detectors have $p_x = p_y$, we can write that the projected area of the pixel is therefore $$A_{proj} = (p_x z/f)^2 \quad (7)$$

Figure 7:
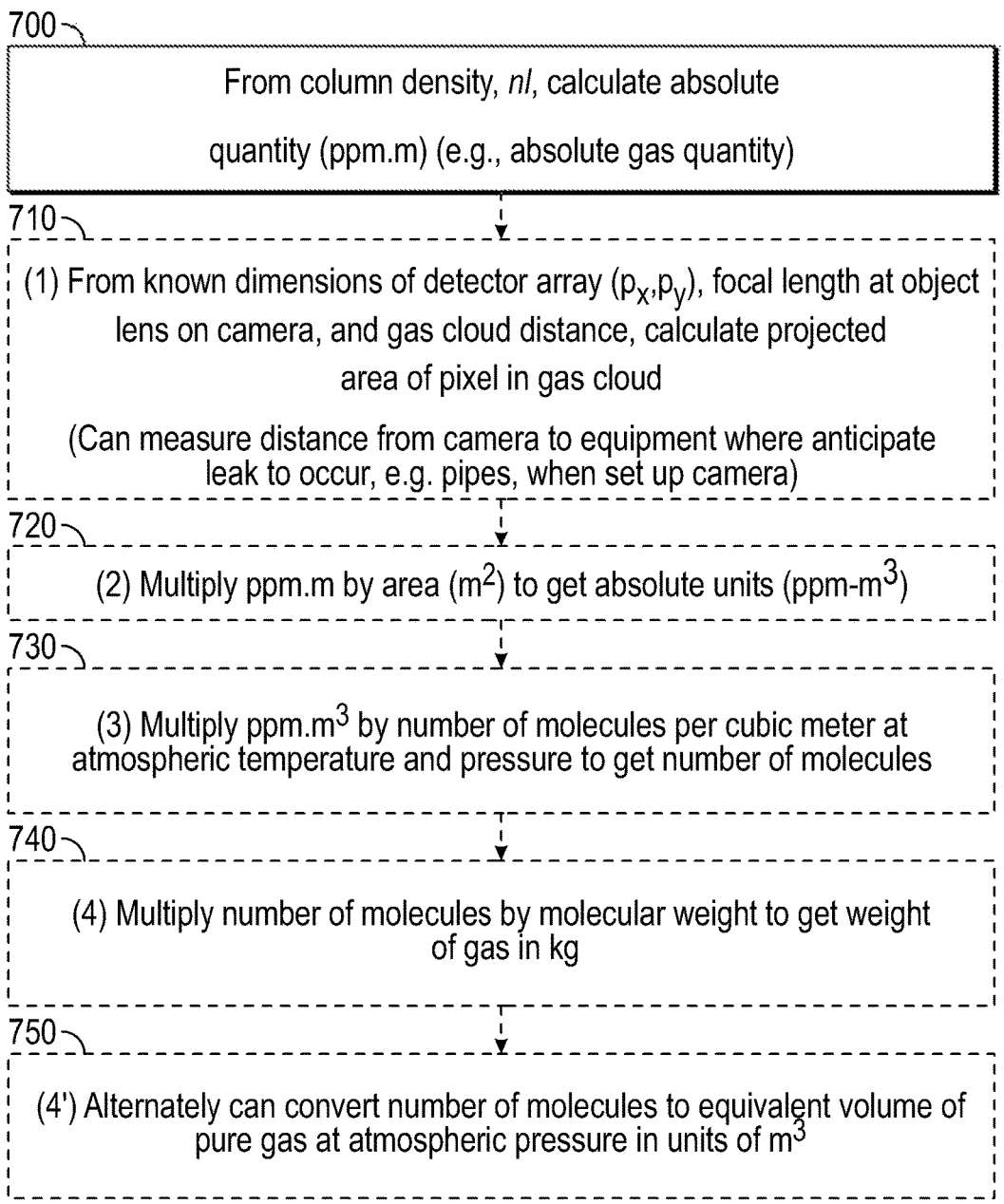
FIG. 7 is a flowchart of an example method for calculating the absolute quantity of gas present in a gas cloud.

FIG. 7 is a flowchart of an example method 700 for calculating the absolute quantity of gas present in a gas cloud. While the pixel dimension $p_x$ and f are known as a result of the hardware design, the gas cloud distance z varies and must be estimated. When setting up a gas cloud imaging camera at a facility, one of the early setup procedures is to measure the distances from the camera to the primary items to be monitored. These items are often things such as a collection of tightly interwound pipes, the wall of a gas container tank, the opening of a gas separator tank, etc. The important thing is that the general region in which potential leaks may occur is known a priori, and thus the distance to any gas leak can be estimated to reasonable accuracy by using that distance as measured during the system setup. As shown in block 710, with distance z known, we can apply (7) to scale the measured gas column density to absolute units. As shown in block 720, simple multiplication leads to units of ppm·m³. But, as shown in block 730, multiplying this result by the number of molecules per cubic meter in standard atmospheric temperature and pressure, and then dividing by $1 \times 10^6$ (because the units is parts per million), we now have a measurement in units of numbers of gas molecules. Since each gas has a known molecular weight, we can also convert "number of gas molecules" directly to kilograms, as shown in block 740, or equivalently to an equivalent volume of pure gas at atmospheric pressure (e.g. units of m³), as shown in block 750.

This calculation gives the absolute gas quantity at each pixel in the image, and if we sum over all pixels in the image we obtain the total volume of gas at one snapshot in time.

While the distance to the gas cloud can be estimated by assuming that the cloud will occur near the equipment being monitored. There are other techniques which are also available. One can use multiple infrared cameras viewing the same scene to triangulate on the gas cloud. Another method is the use a laser tracker (or "laser range finder") tuned to a wavelength that is absorbed by the gas.

6. Emission Rate Quantization

Figure 8:
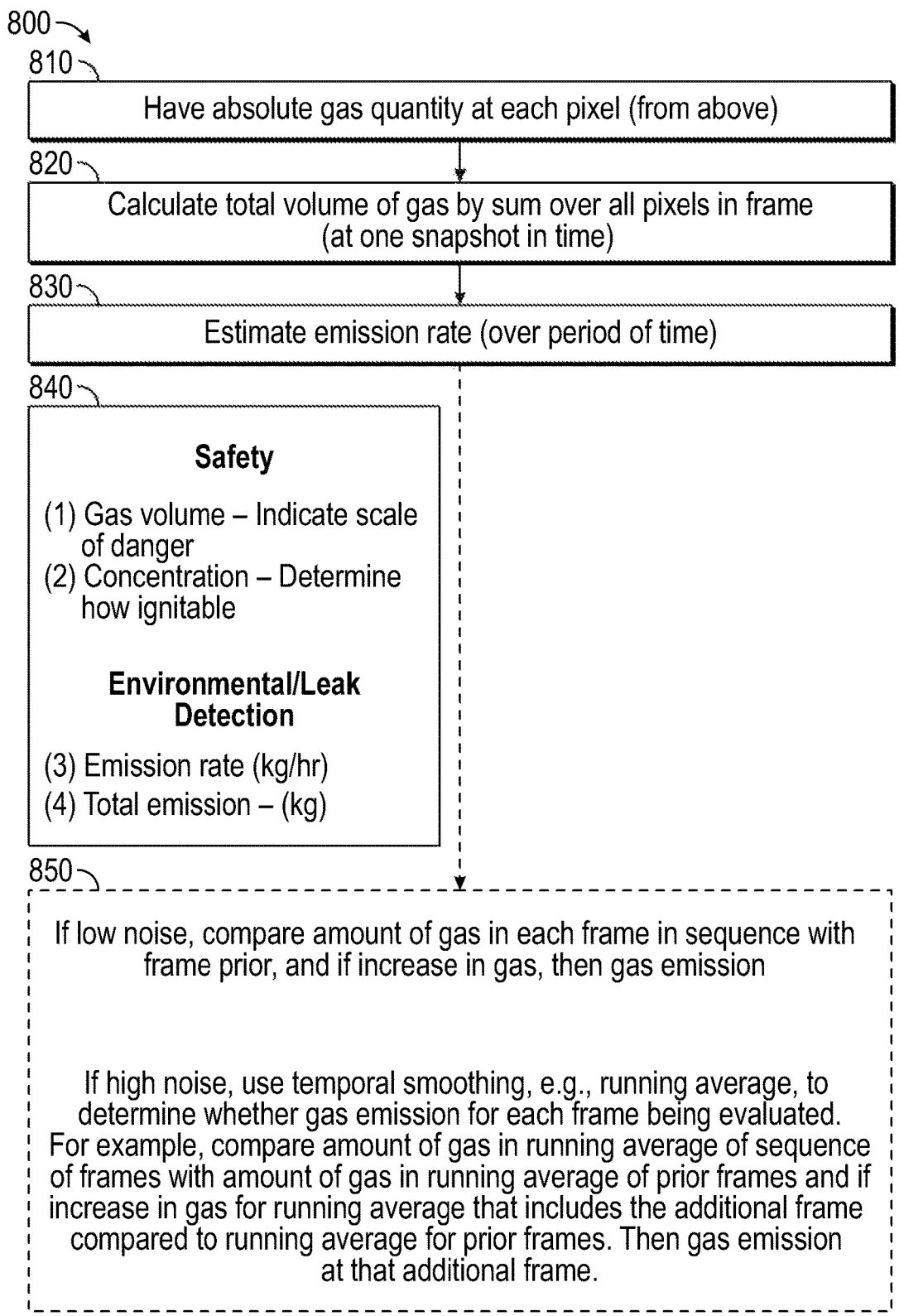
FIG. 8 is a flowchart of an example method for quantizing the emission rate of a gas leak.

FIG. 8 is a flowchart of an example method 800 for quantizing the emission rate of a gas leak. As shown in block 810, the method begins with an estimate of the quantity of gas present at each pixel of the image (which can be determined using the method illustrated in FIG. 5). At block 820, the total volume of gas present in the image can be calculated by summing over all pixels in the frame.

From the previous step, we know the total amount of gas in the scene during each measurement frame. As shown in block 840, from a safety perspective, this measure of the gas volume, and an estimate of its concentration (not column density) are the two most important measures. The former determines the scale of the danger, and the latter determines whether the cloud is capable of igniting. If we are using the gas cloud imager not for safety monitoring but for environmental monitoring or for gas leak detection and repair (LDAR), then the primary quantities of interest are emission rate (units of kg/hr, for example) and total emission (units of kg). At block 830, the emission rate and/or total emission of the gas leak can be calculated. Estimating these quantities requires some additional work.

Researchers have attempted to estimate gas emission rates from gas cloud imaging, but all of the currently published work of which we are aware use supervised methods. That is, they use optical flow techniques to estimate the speed of each tiny parcel of gas within the gas cloud, draw a line or a box somewhere in the image such that the leak source is on one side, and all of the gas passes across the line or box. Not only is this method unsatisfactory from the point of view that it incorporates user supervision or some kind of prior knowledge about the location of the leak source, but optical flow techniques are also computationally intensive and require special care when working with noisy data. We develop a new method that is computationally easy, requires no supervision or knowledge of the leak source location, and can work with surprisingly noisy data.

As shown at block 850, with low-noise data, one could measure the amount of gas present in each frame of a video sequence, and then say that any increase in the gas indicates an emission source. For noisy data, one can use temporal smoothing and look for changes in the temporally smoothed value for total gas present in the scene. Thus, in principle, one need only monitor the steady increase in total gas from the beginning to end of the monitoring period. However, two competing effects work against this. If there is wind in the scene, or if the gas is moving rapidly, then part of the gas cloud may exit the field of view and reduce the total amount of gas in the scene. If this were to happen while a leak were constantly emitting new gas, then the two would compete for each other and the net effect would be no change in total gas observed, and zero estimated gas emission. Thus, we will need to compensate for any gas that leaves the field of view. Secondly, another effect is that some of the gas will drop below the sensitivity limit of the camera. If, for example, there were a momentary leak that created a stationary gas cloud within the scene. As the gas cloud slowly dissipates by mixing with the ambient air, losing concentration but growing in size, the gas cloud imager will lose sensitivity to the lower concentrations and will see a steady decline in the total gas, even though none of it has left the field of view. Clearly, we need to compensate for this effect as well in order to get accurate estimates of gas emission rates.

Figure 9:
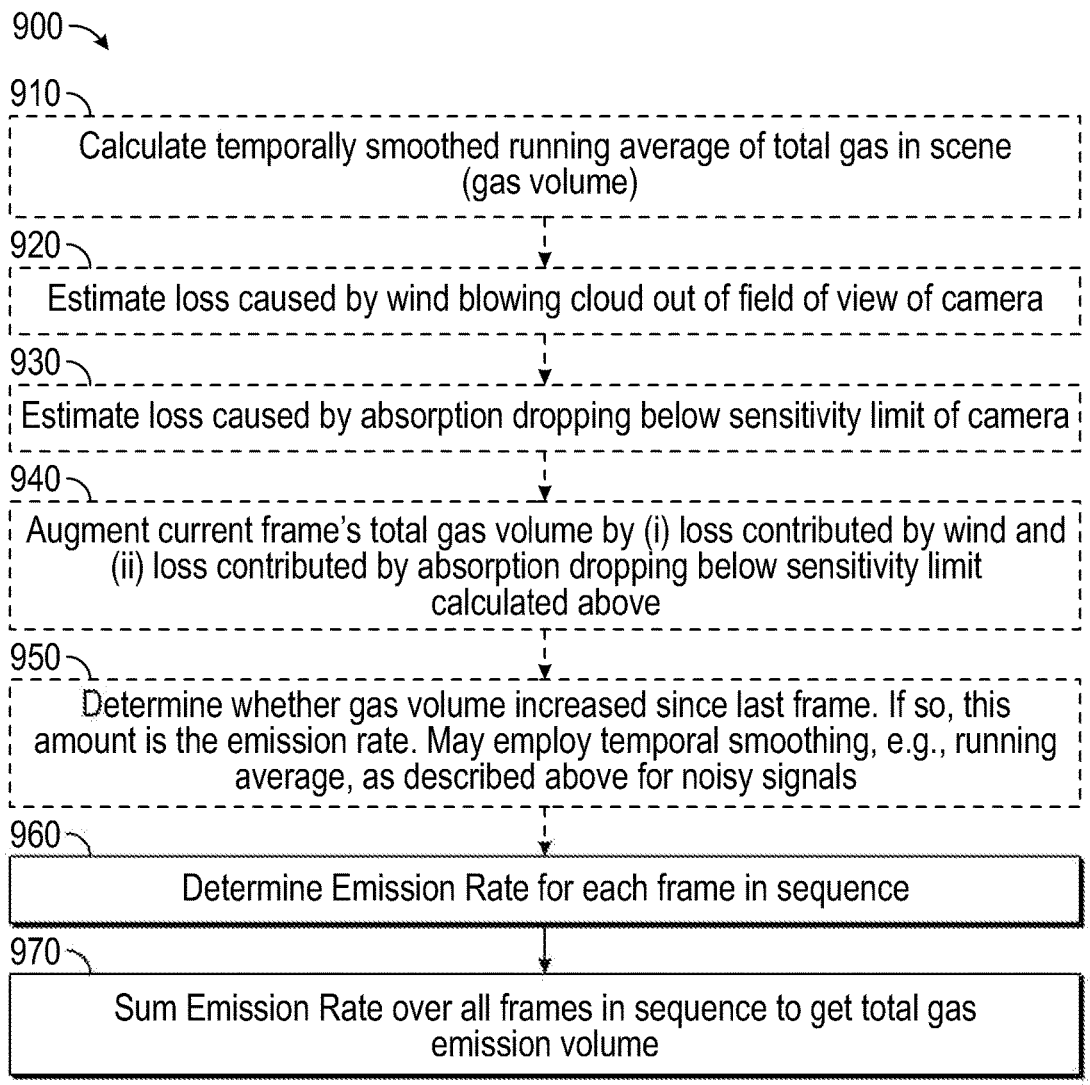
FIG. 9 is a flowchart of an example method 700 for compensating an estimate of emission rate based on gas exiting the field of view of the camera and absorption dropping below sensitivity limits of the camera.

FIG. 9 is a flowchart of an example method 900 for compensating an estimate of emission rate based on gas exiting the field of view of the camera and absorption dropping below sensitivity limits of the camera. As shown at block 910, A temporally-smoothed moving average of the total gas in the scene is efficiently implemented using an exponentially-weighted mean average (EWMA). Using the EWMA the measured gas volume as our best estimate of the true gas volume in the scene, at block 940, we next add our estimate of the amount of gas lost by exiting the field of view (calculated at block 920), and also the amount of gas lost due to dropping below our sensitivity limit (calculated at block 930). From this "augmented" estimate of the current frame's total gas volume, we estimate the emission rate as the amount by which this gas volume has increased since the last frame, as shown at block 950. If this (augmented) gas volume has decreased, then we say that the estimated emission is zero. (That is, the estimate is biased to accept only positive values.)

Estimating the amount of gas that we expect to lose detection to by the time of the next frame is determined using a simple heuristic model that is adjusted to match experimental data. In the model, we first calculate the range of gas column density values detected within the gas cloud. A threshold is set to be some fraction of the range of ppm·m values above the minimum detected value. Thus, if the maximum ppm·m value detected within a gas cloud were calculated as 5000 ppm·m, and the lowest value were 100 ppm·m, then the range would be 4900 ppm·m. If we set a threshold as 20% of the range, then the threshold in units of ppm·m would be $$(\text{ppm·m threshold}) = (\text{minimum ppm·m}) + 0.2 \,(\text{ppm·m range}) = 100 + 0.2(4900) = 1080.$$

Next we locate the set of all "edge pixels" in the gas cloud—all pixels that lie no more than two pixels away from a pixel without gas detected. We expect that some fraction of edge pixels whose column density lies below the calculated threshold will drop below the detection limit of the camera. Using experimental data, we determined that the best value for our camera was 0.25. (As we will see, the final result is usually not very sensitive to the values chosen for use in this heuristic model.) So, say we find all of the edge pixels that lie below the threshold, sum up all of their ppm·m values, and multiply the result by 0.25. This is the total amount of gas we expect to lose sensitivity to by the next frame. Store that value at block 930. When we try to estimate the total gas present in a frame, we will augment it using this value.

Figure 10:
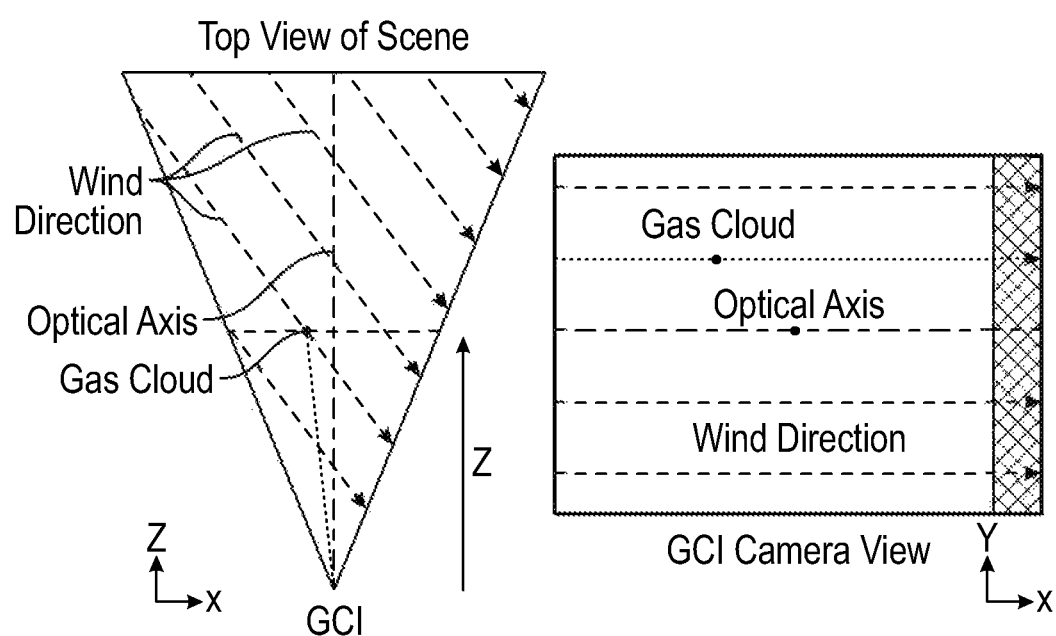
FIG. 10 illustrates a top view of an example scene measured by a gas cloud imager camera, with the gas cloud at a distance z (left).

The next step attempts to estimate how much gas will exit the field of view. This either requires knowing the wind speed and direction in terms of the gas cloud imager's optical axis, or using video analytics to estimate the speed of motion of the gas. FIG. 8 illustrates a top view of an example scene measured by a gas cloud imager camera, with the gas cloud at a distance z (left). FIG. 10 also illustrates the example scene as viewed from the gas cloud imager camera itself (right). The hatched region at the right hand side of the image indicates the area in which any detected gas is expected to leave the field of view by the next frame (due to being pushed out by wind).

If the wind speed and direction are known (for example with an external wind gauge that communicates with the camera), then we can calculate the projection onto the image and estimate the amount that the gas will move in terms of pixels in the image. For example, say we find a result that the wind motion will cause the gas to move 2 pixels in the horizontal direction and 0 pixels in the vertical. At block 920, in order to estimate the amount of gas we expect to lose detection to by the time of the next frame, we need only sum the total amount of gas that lies within the 2-pixel band next to the edge of the image. (This is the hatched region shown in FIG. 10.) For normal situations, the wind speed is such that the number of pixels of motion before the next frame (when imaging at 15 Hz) is less than 2 pixels, so that interpolation of the pixel values is important.

The method 900 above provides an estimate of the gas emission rate, for each frame within the video sequence, as shown at block 960. If we sum over all of the images within the sequence then we obtain the total gas emission volume, as shown at block 970, providing the second of the quantities of interest for environmental and leak detection and repair (LDAR) monitoring.

C. Gas Cloud Imager Software Interface

Figure 11:
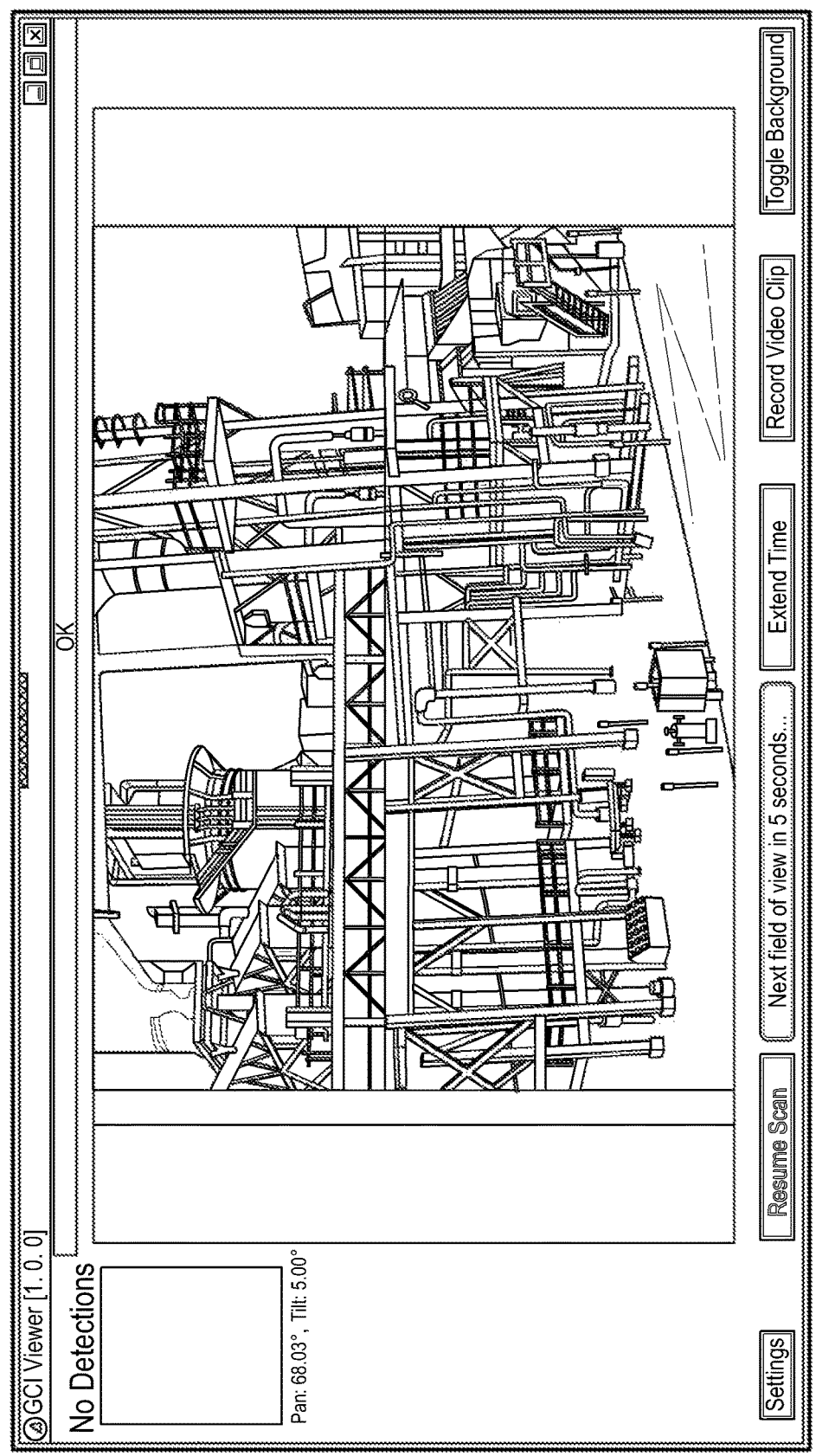
FIG. 11 shows an example of the gas cloud imager (GCI) live viewer graphical user interface.

FIG. 11 shows an example of the gas cloud imager (GCI) live viewer graphical user interface. The interface includes a manual record button toward the lower right. Recorded videos can be uploaded to a webserver for easy viewing from a web browser or downloading to a local computer. The interface also includes a countdown bar that informs the operator when the camera is ready to move. To extend time at a particular field of view, an operator can click on the "Extend Time" button to the right of the countdown bar. The system automatically resumes its scan after the extended time period is finished. If the operator wants to scan before the extend time has finished he/she can click on the resume scan button.

Figure 12:
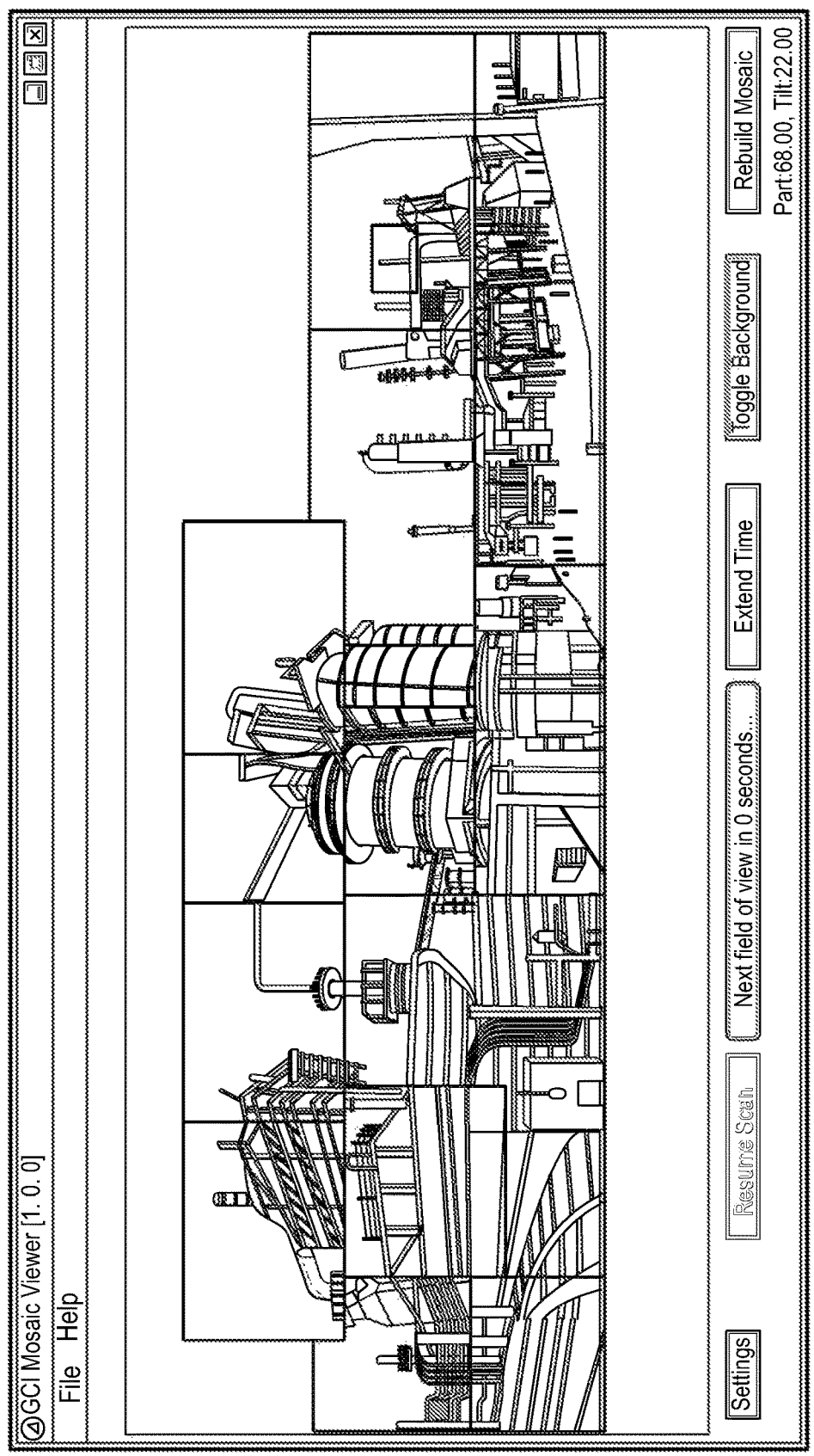
FIG. 12 shows an example of the mosaic viewer interface which shows an overview of the entire area being monitored.

FIG. 12 shows an example of the mosaic viewer interface. The GCI's mosaic viewer can be located right next to the live viewer on a separate monitor and displays the entire monitored area, as shown in FIG. 12. Operators can move the camera to any location in the monitored area by simply clicking on that portion of the mosaic viewer. The camera will stay at that field until the countdown bar has finished (typically 60 secs) and then resumes its automatic motion path. When an alarm has occurred in a particular field a red box will highlight in the mosaic viewer until it has returned to that field and not had an alarm event.

Figure 13:
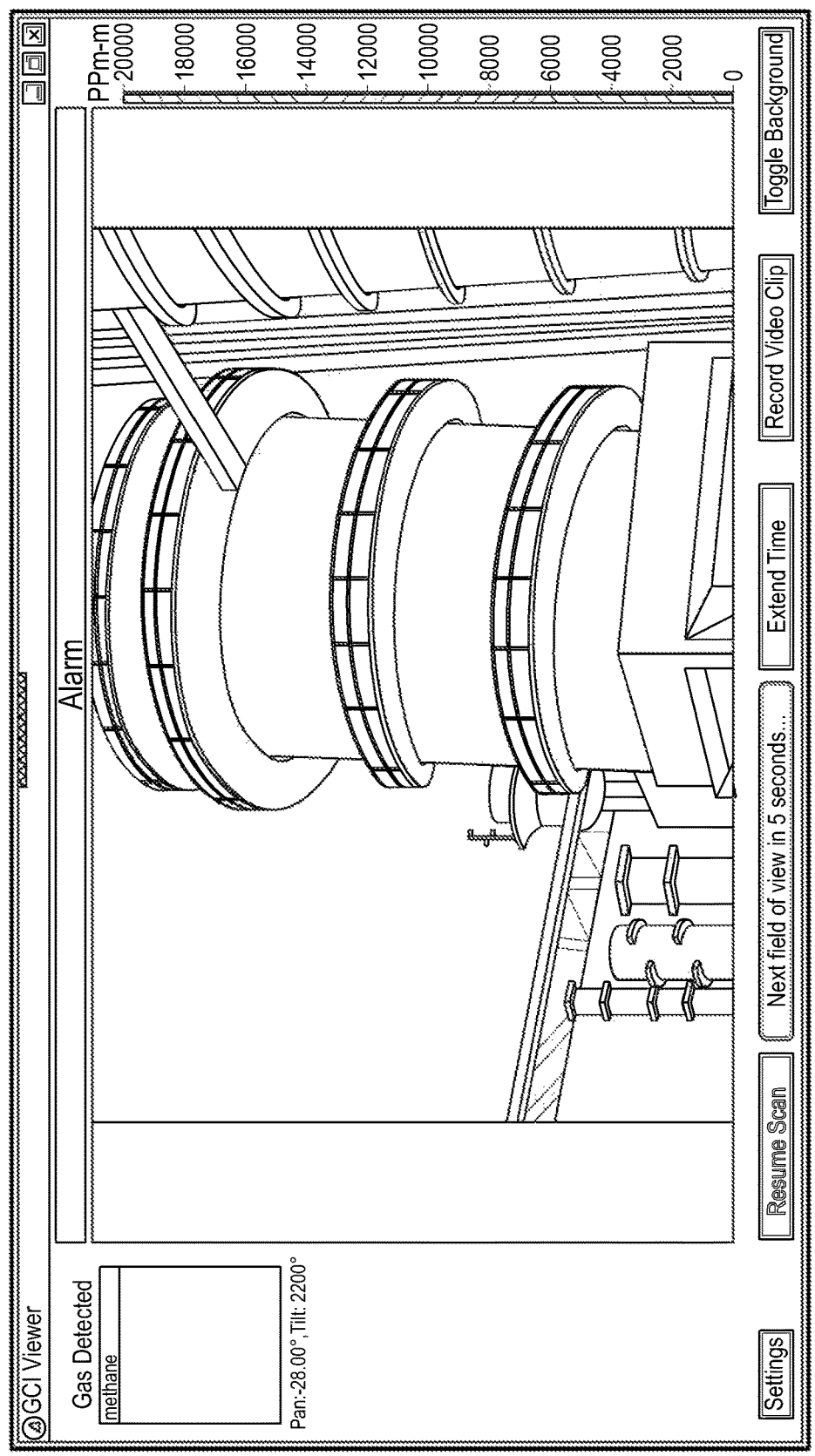
FIG. 13 shows an example of the graphical user interface with an alarm condition.

FIG. 13 shows an example of the graphical user interface with an alarm condition. In the event of an alarm, several notifications occur in the software interface as shown in FIG. 13. First, the banner at the top of the Live Viewer changes to RED. Second, the detected gas is shown in the Gases Detected List. Third, a concentration color bar in ppm-m units is displayed to the right of the viewer. And fourth, the gas cloud is false colored in terms of its concentration and shown in real time on the live viewer screen. Behind the scenes, an email is also sent out to all users with a link to view the gas release from the web server.

Figure 14:
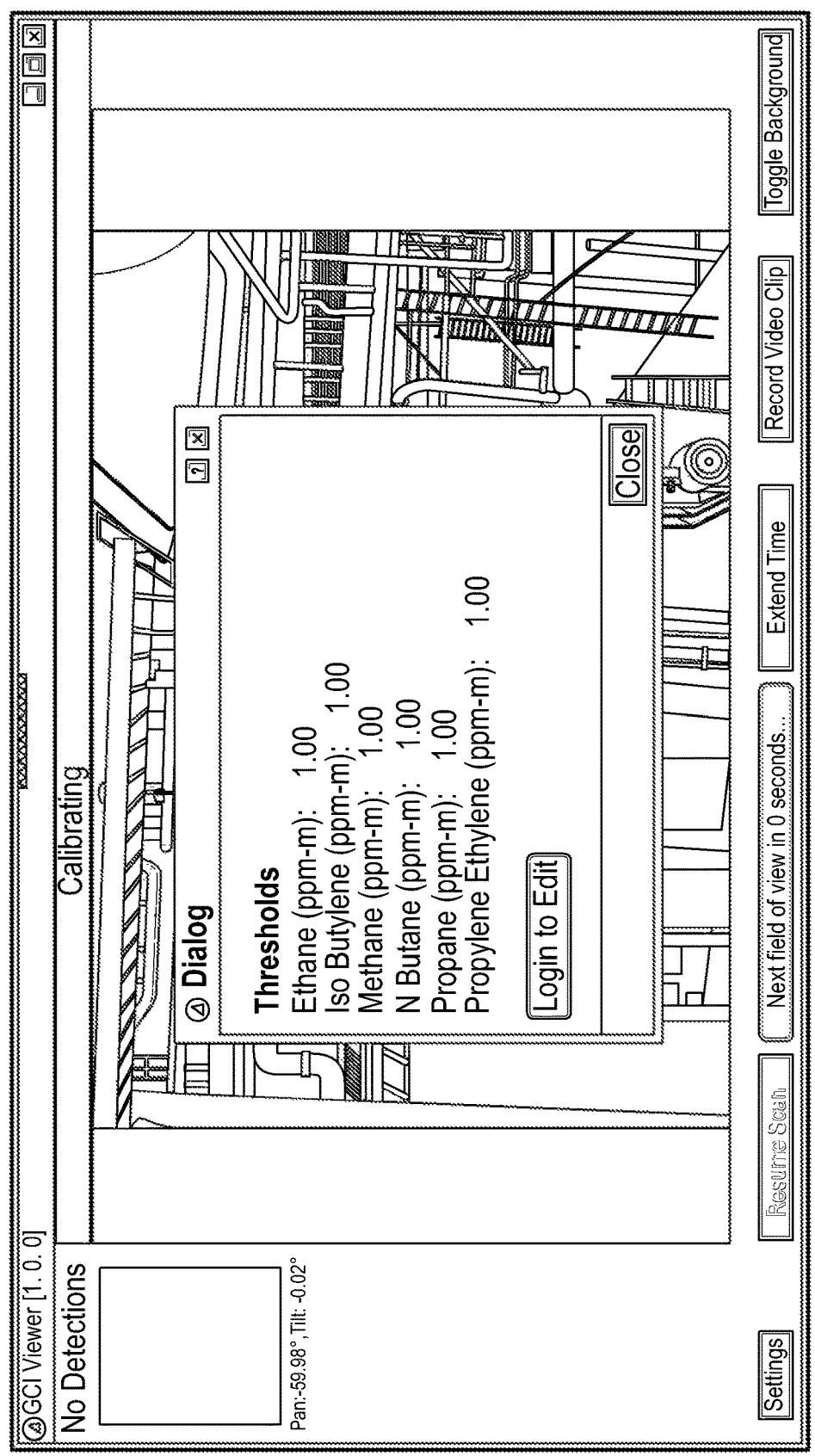
FIG. 14 shows an example of an alarm thresholds settings window.

FIG. 14 shows an example of an alarm thresholds settings window. At any time an operator can view the alarm thresholds for each gas being monitored by clicking on the settings button in the lower left corner of the live viewer, as shown in FIG. 14. To adjust the thresholds an authorized user can login to the dialog window and adjust the thresholds from the same dialog window.

D. Additional Embodiment of Gas Leak Quantification with a Gas Cloud (Video-Rate Infrared) Imager The gas cloud imager (GCI) system uses low-resolution spectroscopy to achieve higher SNR than available with high-resolution spectroscopy. While this has the disadvantage of making the system less capable of discriminating among different spectra, it also has the important advantage that it is less sensitive to saturation. That is, in high-resolution spectroscopy, the sharp absorption/emission features of gases will tend to saturate (i.e. $e^{-\alpha} \neq \alpha$ for absorption coefficient $\alpha$) even on smaller gas clouds. With low-resolution spectra, however, saturation of these features tends to have little effect on the overall intensity across a measured spectral channel because the sharp features tend to be too small to dominate the signal. As a result, one can often ignore saturation effects entirely when working with low-resolution spectra.

1. Introduction

There is a real need to develop an algorithm oriented towards real-time autonomous operation. In brief, various spectral infrared gas detection algorithms may operate roughly as follows. The algorithm monitors the pixel in the scene and looks for spectral radiance changes. Changes that correspond closely to spectral features of a known gas are classified as a detection, and quantification of the pixel's gas column density follows. Summing and scaling all detected pixels within an image provides an estimate of the total cloud volume, so that tracking the total gas volume over a sequence of frames allows for emissions monitoring. Thus, one can think of a certain hierarchy to the measurement sequence. The primary task is simple detection—the most important thing is to determine whether a gas cloud is present, what gas it is made of, and where it is. The secondary task is concentration estimation and quantification—we want to know how much gas is present and what hazards the detected gas poses. The tertiary task is to monitor the gas overtime and form an emission rate estimate.

In the discussion below, we present the measurement model that the algorithm is based on and compare it with the similar model typically used in the existing literature. After providing practical details for implementation and quantification, we compare the results of lab and open-air outdoor experiments to known gas quantities to verify the accuracy of the method. Finally, we also provide examples of the algorithm operating on live data streams.

2. Measurement Model

Figure 15:
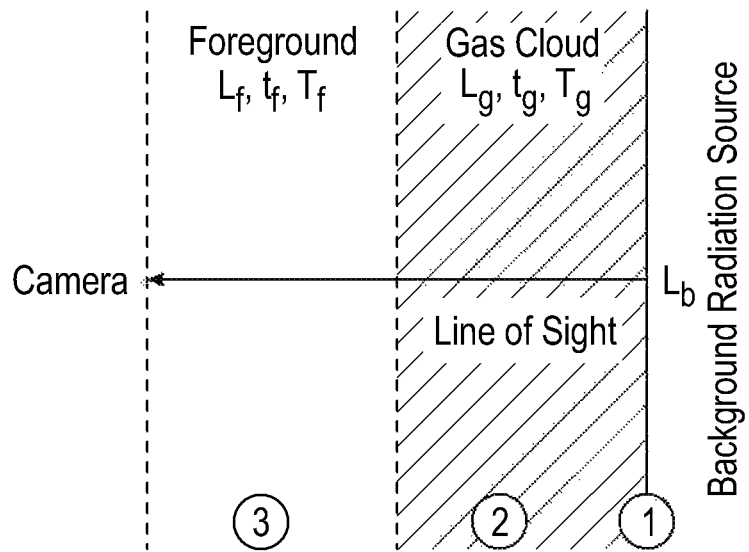
FIG. 15 shows the measurement geometry for a single pixel in a gas cloud imager.

FIG. 15 shows the measurement geometry for a single pixel in a gas cloud imager. The camera line of sight views (1) the background infrared radiation through (2) a gas cloud layer and (3) a foreground atmospheric layer. The gas cloud measurement model is a two-layer radiative transfer system (FIG. 15), in which (1) spectral radiance is generated within a source region which can be either an opaque object such as the ground, or the atmosphere itself, such as when viewing the cloudless sky, or a combination of the two. (2) The source spectral radiance next traverses the gas cloud layer, and is either attenuated or increased by absorption or emission of gases located there. (3) Finally, the radiation passes through a final atmospheric layer before reaching the camera. This measurement model is simpler than the three-layer version often used in the literature, in which there is an additional background atmospheric layer between the gas and an opaque radiation source. The simpler model used here reflects the fact that the autonomous algorithm is agnostic to the spectrum of the background light—whether the atmospheric layer behind the gas is absorbing light from an opaque background source or is itself the source of radiation is information that is not used by the algorithm. Following the literature, we do model both the gas and the foreground layers as being homogeneous (uniform in temperature and gas concentration).

In the discussion below, we use the following variable definitions $L_f$, $L_g$, $L_b$: radiances originating from foreground, gas, and background layers M: at-sensor radiance $\tau_f$, $\tau_g$: transmission of foreground and gas layers $T_f$; $T_g$: temperatures of foreground and gas layers Thus, for a pixel in the scene, using the measurement model shown in FIG. 1, we can write the radiative transfer equation of a ray along the line of sight to given at-sensor radiance M of $$M = L_f + \tau_f \varepsilon_g B(T_g) + \tau_f \tau_g L_b,$$

where $\varepsilon_g$ is the spectral emissivity of the gas. Note that all of these quantities have an implicit spectral dependence (i.e. $M \equiv M(\lambda)$ etc.). Using Kirchoff's law and an assumption of local thermodynamic equilibrium, we can also make the substitution $\varepsilon_g \approx 1 - \tau_g$. Since the pixels in the scene can be treated independently, we need not include the pixel's spatial location within the scene as a variable to model, and thus we can drop the (x, y) dependence from all of the variables and consider only a single pixel at a time.

For passive absorption/emission spectroscopy, the absorption values given by taking a measurement spectrum and comparing it with a reference spectrum. In the case of gas cloud imaging, we therefore look for spectral radiance changes in the scene that may indicate absorption or emission by a gas cloud by comparing the current frame against a reference frame. The reference frame may be a frame obtained at a previous point in time, or a kind of running average. We write the measurement at the current frame of the video sequence as $M^{(1)}$ and the radiance measurement of the reference frame as $M^{(0)}$. Next, if the time difference between the current frame and the reference frame is short (e.g. not long enough to allow substantial changes in background radiance) then we can take the background and foreground quantities as constant, while the gas concentration itself varies on shorter timescales:

$$M^{(0)} = L_f + \tau_f(1 - \tau_g^{(0)}) B(T_g) + \tau_f \tau_g^{(0)} L_b,$$

$$M^{(1)} = L_f + \tau_f(1 - \tau_g^{(1)}) B(T_g) + \tau_f \tau_g^{(1)} L_b.$$

Empirically, we find that a useful timescale for this is on the order of 1 or 2 minutes, beyond which background radiance changes begin to have a significant influence on the estimated absorption value. Thus, the reference spectral radiance $M^{(0)}$ is reset approximately every 1~2 minutes to minimize error. (Section 3 below discusses methods for obtaining $M^{(0)}$.) Taking the difference between the current and reference frames and simplifying leads to $$\Delta M = M^{(1)} - M^{(0)} = -\tau_f(\tau_g^{(1)} - \tau_g^{(0)})[B(T_g) - L_b], \quad (1)$$

where we use $\Delta L$, which equals $L_b$, for the "radiance contrast" between the gas cloud layer and the background. The sign of the radiance contrast indicates whether the cloud is observed in emission ($\Delta L > 0$) or absorption ($\Delta L < 0$). Next, we can correlate the measured spectral radiance change at the sensor $\Delta M(\lambda)$ With the known spectral shape of various library gases, and if the correlation is high enough, and the spectral radiance changes large enough to warrant the change being a result of true signal and not noise, then the pixel is labeled as a "detection" and we can continue on to quantify the detected gas. As we will see below, a low signal strength can result from either a low gas concentration or a poor radiance contrast, and in the latter case it is difficult to obtain an accurate estimate of the concentration, so that one can either assume a concentration of 0 or use spatial and temporal correlations in the data to infer the concentration at a pixel given the value at its neighbors. (Note that spatial-temporal correlations among gas cloud pixels can extend across large regions of the image, and over many frames of data, so that more than just the nearest neighbors can be used to infer the concentration at an unknown pixel.)

Figure 16:
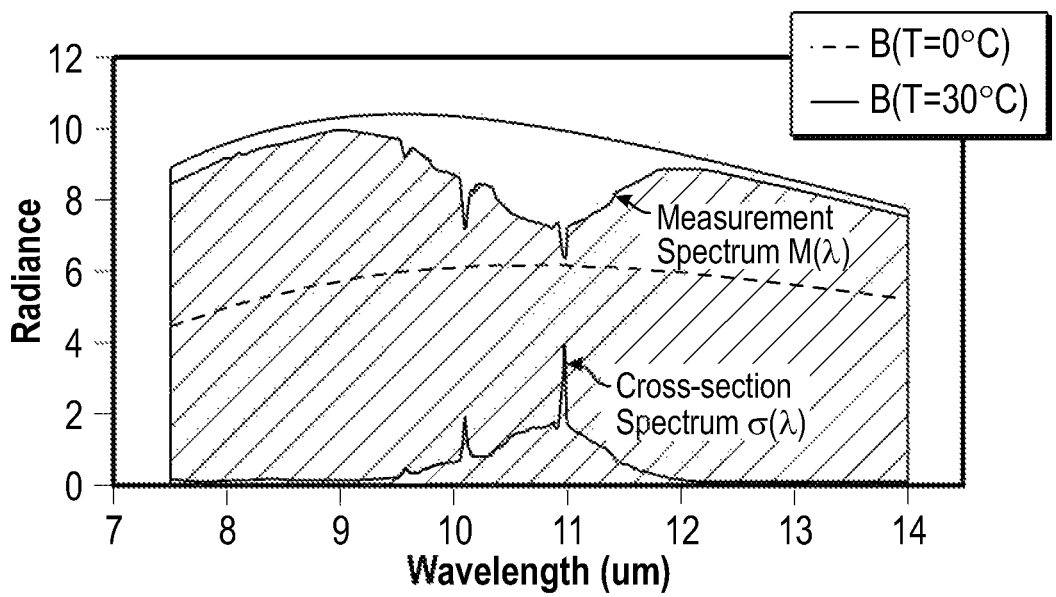
FIG. 16 shows an example absorption spectrum measurement for propylene gas, showing the measured spectrum $M(\lambda)$.

FIG. 16 shows an example absorption spectrum measurement for propylene gas, showing the measured spectrum $M(\lambda)$. When the background sources a black-body at $T_b=0°$ C., the gas temperature is at $T_g=30°$ C., and the gas column density produces a peak absorption value of $A=0.95$ (i.e. $T=0.05$). Note that the measurement spectrum shows a somewhat different shape than the cross-section spectrum due to the nonlinearity of the relation between absorption and cross-section ($\alpha = 1 - e^{-\sigma n l}$).

Once a gas cloud is detected, we can next go on to determine the gas quantity within the pixel. Equation 1 relates the transmission of the gas layer to the measured changes in radiance at the sensor. Using the Beer-Lambert-Bouguer law, the transmission is related to the concentration and size of the gas as $$\tau_g = \exp\left[-\sigma\left(\int_0^l n(z)dz\right)\right] \approx \exp(-\sigma n l),$$

where $\sigma$ is the absorption cross-section, n the gas concentration (number density), and l the path length through the gas. The above approximation becomes valid when the gas layer is approximately homogeneous. Since the measurement involves an integral through the gas layer, it is difficult to separate the contribution of the gas concentration n from the cloud path length l using the radiance value alone, and so we group these two together into a single quantity—the column density $\zeta = nl$.

When the gas concentration is low, the transmission can be modeled with a linearized version of the Beer-Lambert-Bouguer equation obtained by Taylor expansion:

$$1 - \tau = 1 - e^{-\alpha} = \alpha + \frac{1}{2!}\alpha^2 + \ldots \approx \alpha \quad (2)$$

so that $\alpha = -\sigma\zeta$. From (1), the quantity we use during measurement is $(\tau_g^{(1)} - \tau_g^{(0)})$, which in the thin gas approximation gives $$\tau_g^{(1)} - \tau_g^{(0)} \approx \alpha^{(0)} - \alpha^{(1)} = \sigma\zeta^{(0)} - \sigma\zeta^{(1)} = -\sigma\Delta\zeta$$

The change in gas column density $\Delta\zeta$ is the quantity we are looking for. Substituting the above equation into (1), we obtain our estimate of the column density in terms of the measured radiance change and estimated background radiance:

$$\Delta\zeta = \frac{-\Delta M}{\sigma\tau_f[L_b - B(T_g)]}. \quad (3)$$

Finally, we can estimate the background radiance $L_b$ by substituting an hour measurement of the reference radiance value $M^{(0)}$, so that the final equation becomes $$\Delta\zeta = \frac{-\Delta M}{\sigma\tau_f[M^{(0)} - B(T_g)]}. \quad (4)$$

All of the variables on the right-hand side of the equation are quantities that we can estimate. The temperature of the gas $T_g$ is commonly assumed to be equal to that of the ambient air, under the assumption that the gas quickly entrains into the local air. For long wave infrared wavelengths (8-12 μm) systems, the important quantities that typically impact $\tau_f$ for path lengths less than 1 km are those of water vapor and dust. Ignoring the presence of spatially-dependent water vapor variation caused by steam, fog, or rain, the overall average concentration of water vapor in the ambient air can be estimated with a humidity sensor, so that together with an estimate of the distance to a gas cloud, one can then estimate $\tau_f$. For shorter measurement distances, and for those guesses whose absorption features like completely outside the water band, $\tau_f$ can be taken as equal to 1. Finally, the value for a is determined from the type of gas detected, and can be obtained from a spectral library, such as the NIST Infrared Database.

An assumption made in going from (3) to (4) is that the reference spectral radiance $M^{(0)}(\lambda)$ Is an accurate representation of the background spectral radiance $L_b(\lambda)$. Section 3 provides details on how this can be achieved in practice. A second assumption used is that the quantity of interest is the relative change in absorption and not the absolute absorption value. This makes the system agnostic to the spectral shape of the background source. For continuous monitoring situations in outdoor environments, this is an important feature, since many environmental effects—rain, wind-induced motion of partially reflecting surfaces such as tree leaves and man-made signs—create spectral features that can be confused with gas spectral features when evaluated with low-resolution spectroscopy. And low-resolution spectroscopy is, in turn, important for providing the camera with measurements of sufficient SNR to apply the gas detection algorithms. One can say that this approach prioritizes detection above that of quantification, so that it allows detection to take place under a wide set of possible conditions, but allows the estimated gas column density to have more error.

Equation 4 provides the relationships between the change in gas column density $\Delta\zeta$, the measured radiance properties, and the known gas absorption spectrum $\sigma(\lambda)$. However, there are two basic methods for implementing the estimates with an algorithm. The first technique is to average the measured absorption $\Delta M/[M^{(0)} - B(T_g)]$ over one or more spectral bands in which the gas absorption cross-section is significant (i.e. not close to zero). If the other quantities on the right-hand side of (4) are likewise averaged across the same bands, then one obtains an estimate for $\Delta\zeta$ with minimal computational effort. A second technique is to use a statistical method to set the gas cross-section spectrum to the measured absorption spectrum, which is more accurate but involves careful regularization in the presence of noisy data and (especially) background clutter.

In the presence of multiple gas species, each of which is weakly absorbing, the overall absorption can be written as a linear sum over the component observances of each species. Thus, for N gases, in the thin gas and homogeneous layer approximations $$\tau_{mix} = \exp\left[-\sum_{i=1}^{N} \sigma_i \left(\int_0^l n_i(z)dz\right)\right] \approx \sum_{i=1}^{N} \sigma_i n_i l. \quad (5)$$

If the ratios of the various constituent species within the gas mixture remain constant, then the gas mixture can be characterized with single effective cross-section: $\tau_{mix} = \bar{\sigma} \cdot \bar{n} \cdot l$. Thus, while one may use spectral unmixing and matched filtering algorithms to estimate the column densities of multiple gases simultaneously, we limit the current example to gases in which the mixture ratios are constant, and so can be modeled with a single effective absorption cross-section.

So far all of the discussion has been in terms of absorption, that if the radiance emitted by the gas is brighter than that of the background, then we use emittance $\epsilon$ in place of absorption $1-\tau$, but the equivalence between the two under Kirchoff's law means that the only change to the result is a change in sign. Thus, we can use the same expression for emission as for absorption, where $\Delta M$ will be positive in the case of observing the gas in absorption, and negative when observing in emission. An important case where observation of gas is commonly seen in emission is that of a sky background. Not only does the sky occupy a large portion of the field of view in many situations, but it also can have a large radiance contrast. A clear blue sky background can provide over 100 degrees of thermal contrast for most spectral bands across the 8-12 μm spectral range.

3. Estimating the Reference Spectrum of a Scene Pixel

The previous section left out a discussion of how to obtain a good model for the reference spectrum of a scene pixel. One simple way of doing this is to take the reference spectrum as that of a pixel at an initial point in time, $M^{(0)}(\lambda) \equiv M(\lambda, t_0)$, before the measurements themselves begin. For clarity, we show the explicit $\lambda$-dependence here, and we will also write the reference at-sensor radiant spectrum as $\bar{M}$ rather than $M^{(0)}$ to make explicit the fact that we are using a temporal mean for the reference spectrum. In order to improve the SNR of $\bar{M}$, one can of course take the mean spectrum from the first N+1 frames of data rather than just the frame: $\bar{M}(\lambda) = \langle M(\lambda, t) \rangle_{t=t_0, \ldots, t_{N-1}}$. Taking this another step further, one can use a continuously updated running mean, and we have found empirically that this provides good results.

However, while the running average improves detection by improving SNR, problems can occur. Any moving object (such as a car, or a bird) that enters the scene will likely have a radiance very different from that of the background, and so the algorithm might choose between either discarding the existing reference spectrum for the new, incorporating the change into the running mean update, or of maintaining the existing reference and ignoring the update in this case. Since such objects are moving, they produce rapid radiance changes across those pixels that they obscure, and so we find that in practice it is better to maintain the existing reference without performing an update in this case. The trick is to find a criterion by which to discriminate between objects that have moved in front of the background, thereby obscuring it—in which case an update should not be performed—and a change to the background itself—in which case the update should be performed. Another problem that can occur with a running update is that if a gas cloud is present in a scene, then its spectral signature can quickly get "burned into" the reference spectrum, so that the system loses sensitivity. We also want a criterion to minimize this from occurring.

The method we use is an SNR threshold based masking of the update procedure. That is, along with the reference spectrum of the pixel, we also calculate a running estimate of the variance of each spectral channel of the pixel. Taking the ratio of the running mean with the square root of the running variance estimate gives an SNR value at each spectral channel. The above algorithm therefore becomes, in pseudocode, while new_data:

$D = M\_i - M\text{bar}$ $M\text{bar} += D/i$ $B += D*(M - M\text{bar})$ $\text{var}\_M = V/(i-1)$ $\text{SNR}\_M = (M\_i - M\text{bar})/\text{sqrt}(\text{var}\_M)$ where $\bar{M}$ is written as Mbar, and the at-sensor radiance of the current frame as M_i, with i the frame counter. The results var_M and SNR_M are the variance and SNR of the at-sensor radiance. The parameters D and V are the difference value and statistical second moment, used to calculate the variance. For the first second of time in which data is collected, the SNR is calculated over the scene, allowing for all pixels to be updated. Following that, with each new frame we create a binary mask such that for any pixel spectral channel whose SNR value is above a selected threshold, the running update is not applied. This is the simple criterion by which the algorithm determines that a new object has entered the field of view and blocked the background source. For any pixel whose SNR is at or below the threshold, the algorithm applies the running update to $\bar{M}$ and var(M).

4. Estimating the Total Gas Quantity

From Section 2, we can determine whether a gas cloud has been detected in its column density in ppm·m (parts-per-million times meter), or similar units. For emissions monitoring and leak rate estimation, we take a few more steps, the first of which is to convert a gas cloud measurement to absolute quantity units. That is, if we know the effective area of a given pixel, together the column density of gas detected there, then by multiplying the two we obtain the total volume that the gas would occupy if it were a constant 1 ppm·m column density. Dividing by $10^6$ gives the effective volume the pure gas would have at standard atmospheric temperature and pressure. The resulting units can be given as an equivalent volume of pure gas (e.g. L, $m^3$, or $ft^3$), or, by using the known density of molecules at the gas temperature and pressure, one can estimate the total number of molecules in the cloud. Or, more useful still, one can use the molecular mass of the gas to convert the number of molecules to a total mass of gas (g, kg, or lbs).

Figure 17:
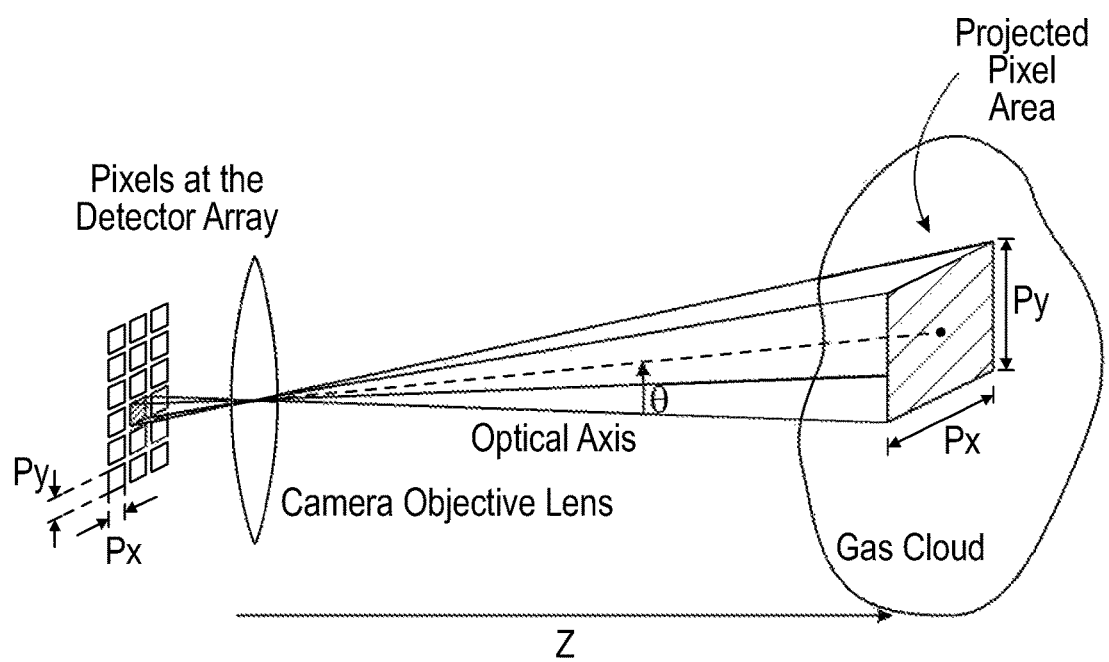
FIG. 17 shows a detector pixel projected to the location of the gas cloud.

The initial step of this calculation, estimating the projected area of a pixel at the cloud, is easily obtained by multiplying the known dimensions of the detector array pixels ($p_x$, $p_y$) by the image magnification, which is a function of the focal length f of the camera objective lens and the distance z to the gas cloud. FIG. 17 shows a detector pixel projected to the location of the gas cloud. We can calculate the projected dimension of the pixel $P_x$ at the plane of the gas cloud as $$P_x \approx p_x z/f.$$

Since most detectors have $p_x = p_y$, we can write that the projected area of the pixel is therefore $$A_{proj}(p_x z/f)^2 \tag{6}$$

While the pixel dimension $p_x$ and f are known as a result of the hardware design, the gas cloud distance z varies and can be estimated. When setting up a gas card imaging camera at a facility, one of the early set up procedures is to measure the distances from the camera to the primary items to be monitored. These items are often things such as a collection of tightly interwoven pipes, the wall of a gas container tank, the valves of a gas separator tank, etc. The important thing is that the general region in which potential leaks may occur is known a priori, and thus the distance to any gas leak can be estimated to reasonable accuracy by using that distance is measured during the system set up.

While the distance to the gas cloud can be estimated by assuming that the gas cloud will occur near the equipment being monitored. There are other techniques which are also available. One can use multiple infrared cameras viewing the same scene to triangulate on the gas cloud. Another method is the use of a laser tracker (or "laser rangefinder") tuned to a wavelength that is absorbed by the gas.

With distance z known, we can apply (6) to scale the measured gas column density to units of equivalent volume of pure gas (L, $m^3$, or $ft^3$) simply by dividing by $10^6$. If the total number of gas molecules is the unit desired, then one can multiply the equivalent pure gas volume by the number of molecules per cubic meter at the ambient atmospheric temperature and pressure. Converting the total number of molecules to the total gas cloud mass then requires only multiplication by the gas' known molecular weight.

5. Emission Rate Quantification

Once we have an estimate of the total gas volume in a video frame, we can then start monitoring the gas volume over many frames in an attempt to estimate the rate at which the gas is being emitted from its source.

What is needed is an autonomous algorithm that is amenable to rapid computation, and which can estimate this loss of sensitivity to the gas as it entrains into the local air. Our approach is to avoid optical flow computations everywhere except the edges of the field of view, and instead to monitor the measured gas volume together with a heuristic estimate of the sensitivity loss from frame to frame. In the vast majority of cases—in which the gas leak source is more than a few pixels away from the edge of the field of view—the sensitivity loss term dominates over the optical flow term. This means that the optical flow calculations can be entirely neglected when the amount of gas near the edge of the field of view is small in proportion to the total gas detected, and this helps to ease the computational burden.

We start by measuring the total amount of gas present in each frame of a video sequence, and then say that any increase in the total gas measured indicates the presence of an emission source, with the increase since the previous frame giving the leak rate. In an ideal measurement environment, this would be all that is needed. The algorithm also monitors the edges of the field of view, so that if there is wind in the scene, or if the gas is moving rapidly due to buoyancy effects, then it can estimate the volume of gas exiting the camera's field of view and add this amount back into the leak rate. Similarly, if any gas enters the field of view from outside, then that portion of the gas volume is subtracted from the leak rate estimate. The final step is to develop a method for measuring sensitivity loss, and augment the leak rate estimate with the corresponding loss term.

Estimating the gas volume decline from frame to frame due to sensitivity limits is determined using a simple heuristic model, developed as follows. The algorithm first calculates the range of gas column density values detected within the gas cloud. The threshold is set to be a fraction of the range of column density (ppm·m) values above the minimum detected value. Thus, if the maximum column density value detected within a gas cloud is 5000 ppm·m, and the lowest 100 ppm·m, then the calculated range is 4900 ppm·m. If we set a threshold as 20% of the range, then the threshold value in units of ppm·m would be $$(\text{ppm·m threshold}) = (\text{minimum } \zeta) + 0.2(\zeta \text{ range}) = 100 + 0.2(4900) = 1080.$$

Next we locate the set of all "edge pixels" in the gas cloud—pixels in a cloud that are no more than two pixels away from a pixel where gas is not detected. We expect that some fraction of edge pixels whose column density lies below the calculated threshold will drop below the detection limit of the camera. Using a series of experimental data, we determined empirically that the best value for our camera was 0.25. Thus, the algorithm locates all of the edge pixels that lie below the threshold, sums up the total gas quantity within them, and multiplies the result by 0.25. This is the total amount of gas we expect to lose sensitivity to by the next frame—the "loss term" that is used to augment the leak rate estimate.

The next step attempts to estimate how much gas will exit the edges of the field of view between the current and the next frame, or how much has entered the field of view from outside it since the previous frame. This either involves knowing the wind speed and direction in terms of the GCI's optical axis, or using video analytics to estimate the speed of motion of the gas. If the wind speed and direction are known (for example with an external wind gauge), then it is a simple calculation to determine the speed in terms of pixels in the image, and estimate gas motion in that way. Wind, however, is generally not as well-behaved as this, so that a unidirectional model of motion will fail to capture the swirls and rapid changes of direction that occur in real life. Thus, estimating flow by modeling the gas motion can be useful for an accurate measure Because flow estimation is known to be computationally intensive, an important means of reducing the size of the problem is to realize that we need only model flow within the outer boundaries of the image, and not the image as a whole.

Once we add the estimated "sensitivity loss" and "flow loss," and subtract the estimated "inward flow" from the current frame's total gas volume, we can track the changes in this "augmented" estimate of the volume from frame to frame. The estimated leak emission rate is the amount by which the augmented gas volume has increased since the last frame. If the augmented gas volume has decreased, then we say that the estimated emission is zero. (That is, the estimate is biased to accept only positive values.) Performing this procedure for every frame over an extended period of observation—such as a 10-second period of a video sequence—the algorithm can obtain the average emission rate over that period.

The embodiments described throughout the attached specification, drawings, claims, and appendix have been described at a level of detail to allow one of ordinary skill in the art to make and use the devices, systems, methods, etc. described herein. A wide variety of variation is possible. Components, elements, and/or steps may be altered, added, removed, or rearranged. For example, method steps shown in the block diagrams can be practiced all together or in any sub-combination. Similarly, claim limitations can be separated and/or combined and included in any combination or sub-combination.

The devices, systems, and methods described herein can advantageously be implemented using, for example, computer software, hardware, firmware, or any combination of software, hardware, and firmware. Software modules can comprise computer executable code for performing the functions described herein. In some embodiments, computer-executable code is executed by one or more general purpose computers (including desktop computers, notebook computers, tablet computers, smart phones, etc). However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers. In addition, where methods are described that are, or could be, at least in part carried out by computer software, it should be understood that such methods can be provided on non-transitory computer-readable media (e.g., optical disks such as CDs or DVDs, hard disk drives, flash memories, diskettes, or the like) that, when read by a computer or other processing device, cause it to carry out the method.

A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

The devices described herein can exchange information with each other, or with other devices, via one or more communication channels. Such communication channels can be wired or wireless, and can include networks, such as a Local Area Network, a Wide Area Network, the Internet, etc.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. An infrared (IR) imaging system for quantifying one or more parameters of a gas cloud, the imaging system comprising:

an optical system including an optical focal plane array (FPA) unit, the optical system having components defining at least two optical channels thereof, said at least two optical channels being spatially and spectrally different from one another, each of the at least two optical channels positioned to transfer IR radiation incident on the optical system towards the optical FPA unit; and a data-processing unit comprising one or more processors, said data-processing unit configured to acquire spectral optical data from the IR radiation received at the optical FPA unit, wherein said data-processing unit is configured to determine absorption spectra data at one or more given pixels of a given frame by comparing spectral data for said one or more pixels of said frame with spectral data from one or more prior frames.

2. A system according to claim 1, wherein said data-processing unit is configured to consider signal to noise as a criteria for determining whether to include data for a particular prior frame in said comparison.

3. A system according to claim 2, wherein said data-processing unit is configured to assess signal to noise based on a standard deviation, variance, or a value based on the standard deviation or variance of the spectral data of a plurality of prior frames at said pixel.

4. A system according to claim 1, wherein said data-processing unit is configured to determine absorption spectra data at one or more given pixels of a given frame by comparing spectral data with a statistical value based on data from prior frames.

5. A system according to claim 4, wherein said statistical value comprises a running average.

6. A system according to claim 4, wherein said data-processing unit is configured to consider noise as a criteria for determining whether to incorporate data for a particular prior frame into the computation of said statistical value.

7. A system according to claim 6, wherein said data-processing unit is configured to assess noise based on variation in spectral data of said prior frames at said pixel.

8. A system according to claim 1, wherein said data-processing unit is configured to determine absorption spectra data at one or more given pixels of a given frame by determining the mathematical difference of said spectral data compared to a running average computed from prior frames.

9. A system according to claim 8, wherein said determining the mathematical difference comprises subtracting radiance spectral data for a pixel for a current frame and a running average of the radiance spectrum for that pixel for prior frames.

10. A system according to claim 1, wherein said spectral data comprises luminance or radiance data.

11. A system according to claim 1, wherein said data-processing unit is configured to compare said spectral data without knowing whether a leak has occurred.

12. A system according to claim 1, wherein the optical system comprises a plurality of IR spectral filters for the different channels.

13. A system according to claim 1, wherein the optical system comprises a plurality of imaging lenses for the different channels.

14. A system according to claim 1, further comprising a display.

15. A system according to claim 1, wherein said data-processing unit is located at least in part remotely from said optical system.

16. A system according to claim 15, wherein said data-processing unit is located at least 10-3000 feet from said optical system.

17. A system according to claim 1, wherein said data processing unit is in operable cooperation with a tangible, non-transitory computer-readable storage medium that contains a computer-readable program code that, when loaded onto the data processing unit, enables the data processing unit to determine absorption spectra data at one or more given pixels of a given frame by comparing spectral data for said pixel of said frame with spectral data from prior frames.

18. The system according to claim 1, wherein the data processing unit is configured to estimate emission rate data for a gas leak using said spectral data.

19. The system according to claim 1, wherein the data processing unit is configured to determine an estimate of gas column density at a selected location within the field of view of the optical system.

20. The system according to claim 19, wherein the data processing unit is configured to determine the estimate of the gas column density at the selected location within the field of view by averaging over one or more spectral bands a plurality of values from a time series of data that correspond to the selected location.

21. The system according to claim 19, wherein the data processing unit is configured to determine the estimate of the gas column density at the selected location within the field of view by fitting a cross-section spectrum of the gas to a plurality of values from a time series of data that correspond to the selected location.

22. The system according to claim 1, wherein the data processing unit is configured to determine an estimate of the total quantity of gas in the gas cloud at a selected location using said spectral data.

23. The system according to claim 22, wherein the data processing unit is configured to determine the estimate of the total quantity of gas at the selected location using knowledge of one or more specifications of the FPA unit, one or more specification of the optical system, distance of the optical system to the gas cloud, or combinations thereof.

24. The system according to claim 22, wherein the data processing unit is configured to determine an estimate the total quantity of gas in the gas cloud at a plurality of locations within the field of view of the optical system and sum said estimates to determine an estimate of the total quantity of gas within the field of view.

25. The system according to claim 1, wherein the sampling rate of the acquired spectral optical data is at least 15 Hz.

* * * * *